US010514340B2

(12) United States Patent
Prusik et al.

(10) Patent No.: US 10,514,340 B2
(45) Date of Patent: *Dec. 24, 2019

(54) DUAL-FUNCTION HEAT INDICATOR AND METHOD OF MANUFACTURE

(71) Applicant: Temptime Corporation, Morris Plains, NJ (US)

(72) Inventors: Thaddeus Prusik, Stroudsburg, PA (US); Dawn E. Smith, Martinsville, NJ (US); Dene H. Taylor, New Hope, PA (US); Raquiba Hoque Arnold, Sparta, NJ (US)

(73) Assignee: TEMPTIME CORPORATION, Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/035,957

(22) Filed: Jul. 16, 2018

(65) Prior Publication Data

US 2018/0321159 A1 Nov. 8, 2018

Related U.S. Application Data

(63) Continuation of application No. 14/943,600, filed on Nov. 17, 2015, now Pat. No. 10,031,086, which is a
(Continued)

(51) Int. Cl.
*G01N 21/78* (2006.01)
*G01K 11/12* (2006.01)
(Continued)

(52) U.S. Cl.
CPC .............. *G01N 21/78* (2013.01); *G01K 3/04* (2013.01); *G01K 11/12* (2013.01); *G01N 31/229* (2013.01)

(58) Field of Classification Search
CPC ........ G01K 3/04; G01K 11/06; G01N 31/229; A61J 9/02; A62B 18/088; A62B 23/02;
(Continued)

(56) References Cited

U.S. PATENT DOCUMENTS 3,247,006 A * 4/1966 Hoge ..................... B41M 5/124
106/31.16
3,999,946 A 12/1976 Patel et al.
(Continued)

FOREIGN PATENT DOCUMENTS

JP 11-140339 5/1999
JP 2008-203065 9/2008
(Continued)

OTHER PUBLICATIONS

International Search Report and Written Opinion of International Searching Authority dated Dec. 2, 2013 issued for International PCT Application No. PCT/US13/40824.
(Continued)

*Primary Examiner* — Sally A Merkling
(74) *Attorney, Agent, or Firm* — K&L Gates LLP

(57) ABSTRACT

A dual-function heat indicator for monitoring two or more modes of heat exposure is described. A manufacturing process for the dual-function heat indicator is also described. Dual-function heat indicators as described may be useful for monitoring the exposure of host products, with which the dual-function heat indicators may be associated, to cumulative ambient heat exposure and to a peak ambient heat exposure, and for other purposes.

36 Claims, 8 Drawing Sheets

Related U.S. Application Data continuation of application No. 13/893,317, filed on May 13, 2013, now abandoned.

(60) Provisional application No. 61/645,889, filed on May 11, 2012.

(51) Int. Cl.
*G01K 3/04* (2006.01)
*G01N 31/22* (2006.01)

(58) Field of Classification Search
CPC    B65D 23/16; C09D 11/50; G01T 1/04; G09F 3/0291; Y10S 252/962
See application file for complete search history.

(56) References Cited

U.S. PATENT DOCUMENTS

| | | | |
|---|---|---|---|
| 4,189,399 A | 2/1980 | Patel | |
| 4,284,719 A | 8/1981 | Agerhem et al. | |
| 4,299,880 A * | 11/1981 | Arens | B41M 5/0029 |
| | | | 346/135.1 |
| 4,384,980 A | 5/1983 | Patel | |
| 4,389,217 A | 6/1983 | Baughman et al. | |
| 4,428,321 A * | 1/1984 | Arens | G01K 3/04 |
| | | | 116/207 |
| 4,551,738 A | 1/1985 | Maruta et al. | |
| 4,753,188 A | 6/1988 | Schmoegner | |
| 4,788,151 A | 11/1988 | Preziosi et al. | |
| 4,789,637 A | 12/1988 | Preziosi et al. | |
| 4,917,503 A | 4/1990 | Bhattacharjee | |
| 5,057,434 A | 10/1991 | Prusik et al. | |
| 5,622,137 A | 4/1997 | Lupton et al. | |
| 5,709,472 A | 1/1998 | Prusik et al. | |
| 5,741,592 A | 4/1998 | Lewis et al. | |
| 5,756,356 A | 5/1998 | Yanagi et al. | |
| 5,822,280 A | 10/1998 | Haas | |
| 6,042,264 A | 3/2000 | Prusik et al. | |
| 6,043,021 A | 3/2000 | Manico et al. | |
| 6,060,426 A | 5/2000 | Tan | |
| 6,410,896 B2 | 6/2002 | Witonsky et al. | |
| 6,524,000 B1 | 2/2003 | Roth | |
| 6,544,925 B1 * | 4/2003 | Prusik | B32B 7/06 |
| | | | 374/E3.004 |
| 6,602,594 B2 | 8/2003 | Miyata et al. | |
| 6,642,016 B1 | 11/2003 | Sjoholm et al. | |
| 6,759,368 B2 | 7/2004 | Lelental et al. | |
| 6,924,148 B2 | 8/2005 | Prusik | |
| 7,019,171 B1 | 3/2006 | Prusik et al. | |
| 7,139,226 B2 | 11/2006 | Haas | |
| 7,161,023 B2 | 1/2007 | Prusik et al. | |
| 7,442,237 B1 | 10/2008 | Gardner | |
| 7,490,575 B2 | 2/2009 | Taylor et al. | |
| 7,517,146 B2 | 4/2009 | Smith et al. | |
| 7,682,830 B2 | 3/2010 | Prusik et al. | |
| 7,891,310 B2 | 2/2011 | Taylor et al. | |
| 8,067,483 B2 | 11/2011 | Prusik et al. | |
| 8,122,844 B2 | 2/2012 | Smith et al. | |
| 8,430,053 B2 | 4/2013 | Taylor et al. | |
| 8,671,871 B2 | 3/2014 | Huffman et al. | |
| 2006/0247967 A1 | 11/2006 | Prusik et al. | |
| 2008/0004372 A1 | 1/2008 | Prusik et al. | |
| 2008/0110391 A1 * | 5/2008 | Taylor | G01K 3/005 |
| | | | 116/216 |
| 2008/0233290 A1 | 9/2008 | Ward-Askey et al. | |
| 2009/0031921 A1 | 2/2009 | Ward-Askey et al. | |
| 2009/0131718 A1 | 5/2009 | Baughman et al. | |
| 2010/0034961 A1 | 2/2010 | Tenetov et al. | |
| 2010/0247900 A1 | 9/2010 | Parker | |
| 2010/0264640 A1 | 10/2010 | Lane | |
| 2011/0086995 A1 | 4/2011 | Castillo Martinez et al. | |
| 2012/0079980 A1 | 4/2012 | Taylor et al. | |
| 2012/0079981 A1 | 4/2012 | Huffman et al. | |
| 2012/0174853 A1 | 7/2012 | Wilson | |
| 2013/0239874 A1 | 9/2013 | Smith et al. | |

FOREIGN PATENT DOCUMENTS

| | | |
|---|---|---|
| JP | 2009-515202 | 4/2009 |
| WO | WO 99/39197 | 8/1999 |
| WO | WO 2007/035365 | 3/2007 |
| WO | WO 2007/118933 | 10/2007 |
| WO | WO 2012/044655 | 4/2012 |

OTHER PUBLICATIONS

Wang, et al., "Thermo-Sensitive Materials for the Time-Temperature Indicator", 2011, Advanced Materials Research, 284-286, 2442.

Office Action dated Mar. 13, 2019 issued for corresponding Korean patent application No. 10-2014-7033160.

* cited by examiner

OD Measurement of Active Region for tests at 90°C (Average of 10 Values)

| Time (sec) | Time (min) | Cumulative Indicator Only | Dual Indicator | Thermal Paper Construction Only |
|---|---|---|---|---|
| 0 | - | 0.13 | 0.21 | 0.18 |
| 1 | - | 0.13 | 1.06 | 0.99 |
| 5 | - | 0.13 | 1.25 | 1.45 |
| - | 8.3 | 0.25 | 1.24 | 1.42 |
| - | 16.5 | 0.34 | 1.23 | 1.36 |
| - | 24.7 | 0.42 | 1.24 | 1.32 |
| - | 33 | 0.51 | 1.26 | 1.32 |
| - | 42 | 0.61 | 1.29 | 1.28 |

FIG. 10

OD Measurement of Active Region for tests at 80°C (Average of 10 Values)

| Time (sec) | Time (min) | Cumulative Indicator Only | Dual Indicator | Thermal Paper Construction Only |
|---|---|---|---|---|
| 0 | - | 0.13 | 0.21 | 0.19 |
| 1 | - | 0.13 | 0.21 | 0.19 |
| 5 | - | 0.13 | 0.21 | 0.19 |
| 10 | - | 0.13 | 1.04 | 1.12 |
| - | 1 | 0.13 | 1.03 | 1.11 |
| - | 48 | 0.23 | 1.15 | 1.28 |
| - | 70.5 | 0.30 | 1.12 | 1.19 |
| - | 177 | 0.68 | 1.26 | 1.14 |

FIG. 11

OD Measurement of Active Region for tests at 50°C (Average of 10 Values)

| Time (hrs) | Cumulative Indicator Only | Dual Indicator | Thermal Paper Construction Only |
|---|---|---|---|
| 0 | 0.13 | 0.21 | 0.19 |
| 1.1 | 0.14 | 0.24 | 0.20 |
| 2.3 | 0.14 | 0.25 | 0.20 |
| 2.9 | 0.14 | 0.26 | 0.21 |
| 3.3 | 0.15 | 0.26 | 0.20 |
| 4.2 | 0.16 | 0.27 | 0.21 |
| 5.0 | 0.15 | 0.28 | 0.21 |
| 6.0 | 0.17 | 0.28 | 0.21 |
| 8.0 | 0.18 | 0.31 | 0.21 |
| 15.0 | 0.21 | 0.35 | 0.21 |
| 32.4 | 0.31 | 0.45 | 0.22 |
| 42.7 | 0.38 | 0.51 | 0.21 |
| 51.0 | 0.42 | 0.55 | 0.21 |
| 76.3 | 0.56 | 0.68 | 0.21 |
| 85.7 | 0.64 | 0.74 | 0.22 |

FIG. 12

OD Measurement of Active Region for tests at 37°C (Average of 10 Values)

| Time (days) | Cumulative Indicator Only | Dual Indicator | Thermal Paper Construction Only |
|---|---|---|---|
| 0 | 0.13 | 0.21 | 0.19 |
| 3.5 | 0.21 | 0.33 | 0.19 |
| 7 | 0.30 | 0.43 | 0.19 |
| 10 | 0.37 | 0.51 | 0.19 |
| 14 | 0.48 | 0.61 | 0.19 |
| 18 | 0.60 | 0.71 | 0.18 |
| 21 | 0.69 | 0.80 | 0.20 |

FIG. 13

Measured Optical Densities

| Temperature (°C) | Cumulative Indicator (HEATmarker VVM14) | Dual Heat Indicator | Peak Indicator (DEGmarker 40) |
|---|---|---|---|
| 25 | 0.16 | 0.55 | 0.65 |
| 35 | 0.16 | 0.55 | 0.62 |
| 45 | 0.17 | 0.94 | 1.93 |

FIG. 14

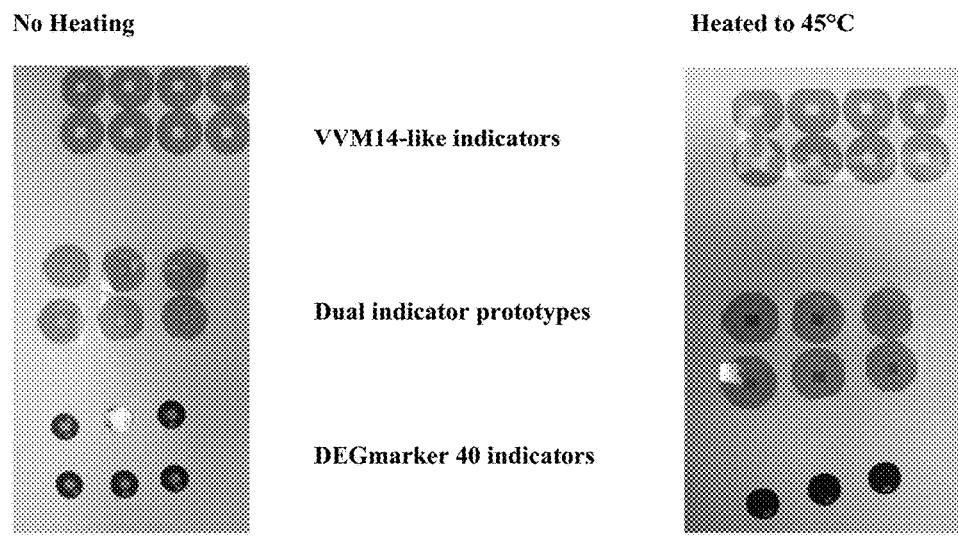

FIG. 15

Appearance of Active Regions in Dual Heat Indicators with either VVM14 DEGmarker 40 or DEGmarker 45

| Temperature (°C) | Appearance of Active Region | |
|---|---|---|
| | Dual Heat Indicator (VVM14 with DEGmarker 40) | Dual Heat Indicator (VVM14 with DEGmarker 45) |
| 38 | Light gray | Light gray |
| 39 | Dark gray | Light gray |

| 40 | Black | Light gray |
|---|---|---|
| 44 | Black | Black |
| 45 | Black | Black |

FIG. 16

Rate of Response of Coated and Uncoated Thermal Substrate to Activator at 43°C

| Sample | Vendor | Product | Type | Initial Static Sensitivity [B](°C) | Appearance after 40 min. at 43°C |
|---|---|---|---|---|---|
| 112 | Kanzaki (1) | P35032 | Uncoated Paper Facestock | 80 | Black areas |
| 113 | Kanzaki | KIP 37032 | Coated Paper Facestock | 80 | No change |
| 114 | Wausau (2) | Ultratherm W004188 | Uncoated Paper Facestock | 75 | Black areas |
| 115 | Wausau | Ultratherm W000037 | Coated Paper Facestock | 85 | Traces of color |

(1) Kanzaki Specialty Papers, Ware MA. (2) Wausau Coated Papers, Wausau WI.

FIG. 17

DUAL-FUNCTION HEAT INDICATOR AND METHOD OF MANUFACTURE

CROSS REFERENCE TO RELATED APPLICATIONS

This application is a continuation of U.S. patent application Ser. No. 14/943,600, filed on Nov. 17, 2015, which is a continuation of U.S. patent application Ser. No. 13/893,317, filed on May 13, 2013, which claims the benefit of U.S. Provisional Patent Application No. 61/645,889 filed on May 11, 2012. The entire disclosures of said applications are incorporated by reference herein for all purposes.

BACKGROUND

Many commercial products are heat-sensitive and may lose efficacy or quality if they experience excessive ambient heat exposure before they are used. Examples of heat-sensitive commercial products include certain pharmaceuticals, medical products, and foodstuffs as well as some industrial products. Accordingly, time-temperature indicators have been provided that may monitor the cumulative ambient heat exposure of a host product and signal when a predetermined value that may correlate with a decline in the condition of the host product has been reached. The signal may be a color change, for example a darkening of an indicator area, and may be generated by a heat-sensing agent such as a diacetylenic compound, or another technology, that integrates the heat exposure, as measured by temperature, over time. Some examples of heat-sensitive diacetylenic compounds, and of time-temperature indicators employing them, are described in U.S. Pat. No. 8,067,483 to Prusik et al.; U.S. Patent Application Publication No. 2009/0131718 by Baughman et al.; and U.S. Patent Application Publication No. 2011/0086995 by Castillo Martinez et al. Other patents and patent publications describing various time-temperature indicator technologies are cited elsewhere herein.

Some host products are also sensitive to short-lived peaks, or spikes, of heat exposure that may not have sufficient cumulative heat value to cause an accompanying time-temperature indicator to signal that a heat exposure limit may have been reached. Some examples of such products are vaccines and other medical products which include a proteinaceous active ingredient.

Accordingly, there is a need for a dual-function heat indicator that may effectively monitor cumulative ambient heat exposure and peak ambient heat exposure and provide a clear signal of possible excess heat exposure.

Various proposals are known for indicators that may signal past exposure to temperatures exceeding a threshold. For example, U.S. Pat. No. 5,709,472, and its divisional patent, U.S. Pat. No. 6,042,264, both to Prusik et al., describe and claim a time-temperature indicator label for measuring the length of time to which a product has been exposed to a temperature above a pre-determined temperature. Also, U.S. Pat. No. 7,517,146 to Smith et al. describes an excess temperature indicator that may provide a visual indication of past exposure of perishable, maturing and other host products to an elevated temperature exceeding a threshold temperature.

Further, U.S. Pat. No. 5,057,434 to Prusik et al. ("Prusik et al. '434" herein) relates to an improved time-temperature indicator device useful in monitoring the environmental exposure of products that undergo progressive quality changes in response to such exposures. See, e.g., column 1, lines 5-8 of Prusik et al. '434. As described, a cumulative time-temperature indicator and a threshold indicator may be integrated into a single device. Further, the device may gradually and irreversibly develop color as a function of time and temperature and more closely monitor the actual condition of a deteriorative product than does a single indicator, See, e.g., abstract of Prusik '434. The capabilities of the system may be enhanced by a barrier layer that delays the color development action. See, e.g., column 9, lines 25-33.

SUMMARY

While the heat exposure indicators described in the foregoing background may be effective for their intended purposes, a need exists for a dual-function heat indicator that may monitor both cumulative ambient heat exposure and peak ambient heat exposure, and which has enhanced properties.

Some commercial products are particularly sensitive to heat and have a small heat capacity so that even brief peaks of excessive heat may be damaging. For example, vaccines are typically packaged in small vials including individual dosages and readily lose potency if their immunogenic proteins are subjected to excessive heat.

Accordingly, a dual-function heat indicator that may signal cumulative ambient heat exposure and exposure to an ambient heat peak of brief duration would be useful to monitor vaccines and other products for potentially damaging heat exposure.

One example embodiment of the invention is a dual-function heat indicator for monitoring cumulative ambient heat exposure and peak ambient heat exposure. The dual-function heat indicator may include a substrate, a cumulative exposure indicator supported by the substrate and a peak exposure indicator supported by the substrate. The cumulative exposure indicator may be supported in a viewable, layered configuration, and may be color-changeable in response to cumulative ambient heat exposure. The peak exposure indicator may also be supported by the substrate in a viewable, layered configuration.

The peak exposure indicator may include a first reactant, a second reactant and a meltable solid. The first reactant may be chemically co-reactable with the second reactant to provide a color change and the meltable solid may physically separate the first reactant from the second reactant. The color-changing chemical reaction may be induced in response to an ambient heat exposure peak, which may be a peak that exceeds the melting point of the meltable solid. For example, melting of the meltable solid caused by the ambient heat exposure peak may bring the first reactant into contact with the second reactant. Such a dual-function heat indicator may indicate cumulative ambient heat exposure and/or peak ambient heat exposure by changing color. Some embodiments may change color in response to any of: cumulative ambient heat exposure reaching a predetermined value; a peak ambient heat exposure event; a combination of the two events; and a combination of two partial events that have a sufficient additive effect. Use of chemical reactants to provide a color change may enable the peak exposure indicator to respond quickly to a relatively brief ambient heat exposure peak, and with appropriate selection of reactants, with a strong color change.

The dual-function heat indicator may also include a viewable active area wherein the cumulative exposure indicator and the peak exposure indicator are viewable with the optical densities of the viewed indicators combined. Thus, the outputs of the cumulative exposure indicator and the peak exposure indicator may be integrated into a single display.

In some example embodiments, the peak exposure indicator may include a peak indicator layer of the dual-function heat indicator and the first reactant and the second reactant may be particulate and dispersed in the peak indicator layer. Including the first reactant and the second reactant, and optionally, the meltable solid in the same layer of the dual-function heat indicator may help provide a quick response as a result of the proximity of the reactants.

The cumulative exposure indicator may be transparent prior to changing color and may be configured in a first layer of the dual-function heat indicator and the peak exposure indicator may be configured in a second layer of the dual-function heat indicator. The second layer may be disposed between the cumulative exposure indicator and the substrate, and the peak exposure indicator may be viewable through the cumulative exposure indicator when the latter is transparent.

In another example embodiment of the dual-function heat indicator, the cumulative exposure indicator is configured in one layer and the peak exposure indicator is disposed in the same layer as the cumulative exposure indicator.

In a further example embodiment of the invention, a meltable colored material that has a small particle size and is initially light-colored due to light scattering, and which darkens upon melting, may replace the first reactant and the second reactant. Alternatively, the material may reveal or obscure a background color upon melting, resulting in a change of the visual appearance of an indicator.

Another example embodiment of the invention is a heat indicator for monitoring ambient heat exposure traversing a threshold temperature that employs a coalescable particulate colored material that has a small particle size and is initially light-colored due to light scattering, and which darkens in response to an ambient heat exposure event traversing the threshold temperature. The threshold temperature may be a peak temperature, a freezing temperature or another suitable temperature.

Another example embodiment of the invention is a method of making a dual-function heat indicator for monitoring cumulative ambient heat exposure and peak ambient heat exposure. Optionally, the dual-function heat indicator may be the example embodiment described previously herein. The method may include applying a liquid composition including a cumulative heat-sensing agent to a substrate. The cumulative heat-sensing agent may be color-changeable in response to cumulative ambient heat exposure and may be transparent prior to changing color. Further, the method may include drying the liquid composition on the substrate to provide a dried composition, without changing the color of the heat-sensing agent, and incorporating a peak exposure indicator composition in the liquid composition. The peak exposure indicator composition may include a first reactant, a second reactant and a meltable solid.

Drying may be conducted at a relatively low temperature, for example, a temperature below the melting-point of the meltable solid, such as a temperature below about 40° C. or below about 30° C. Forced convection, control of the humidity of the air or gas flow, and/or limiting the duration of the drying may optionally be employed to assist drying and avoid changing the color of the heat-sensing agent. Other useful drying techniques that may be employed and which may be performed at a suitably low temperature include radiation curing, for example using ultraviolet light or electron beam energy.

As an alternative to incorporating a peak exposure indicator composition in the liquid composition, the method may include supporting a peak exposure indicator including a first reactant, a second reactant and a meltable solid on the substrate, prior to the application of the liquid composition, and applying the liquid composition over the peak exposure indicator on the substrate.

In some example embodiments of the method, the first reactant and the second reactant may be chemically co-reactable to provide a color change, the meltable solid may physically separate the first reactant from the second reactant in the dried composition, or in the substrate-supported peak exposure indicator, and/or the color-changing chemical reaction may be induced in response to an ambient heat exposure peak.

Another example embodiment may include applying the peak exposure indicator composition to a discrete area of the substrate prior to applying the liquid composition, and applying the liquid composition to the entire area of the peak exposure indicator. The substrate may bear a coating of the peak exposure indicator composition and the coating may, optionally, extend over the entire area of the substrate.

An alternative method of manufacturing may have the cumulative and peak indicators prepared separately as described above, and then being combined by lamination.

In practicing some example embodiments of the invention, the first reactant and the second reactant may be particulate and the liquid composition may include an aqueous dispersion of the first reactant, the second reactant and the meltable solid.

In one example embodiment of the dual-function heat indicator for monitoring cumulative ambient heat exposure and peak ambient heat exposure, the dual-function heat indicator may include a substrate, a cumulative exposure indicator supported by the substrate in a viewable, layered configuration, the cumulative exposure indicator being color-changeable in response to cumulative ambient heat exposure, and a peak exposure indicator supported by the substrate in a viewable, layered configuration, the peak exposure indicator may include a first reactant, a second reactant and a meltable solid, the first reactant being chemically co-reactable with the second reactant to provide a color change, the meltable solid physically separating the first reactant from the second reactant, and the color-changing chemical reaction being induced in response to an ambient heat exposure peak temperature exceeding the melting point of the meltable solid wherein the dual-function heat indicator indicates at least one of cumulative ambient heat exposure and peak ambient heat exposure by changing color.

Optionally the example embodiment of the dual-function heat indicator may include a viewable active area wherein the cumulative exposure indicator and the peak exposure indicator are viewable in the active area with the optical densities of the viewed indicators combined. Further, in the example embodiment of the dual-function heat indicator the peak exposure indicator may include a peak indicator layer where the first reactant and the second reactant are particulate and are dispersed.

Alternatively, the example embodiment of the dual-function heat indicator may include a cumulative exposure indicator which may be transparent prior to changing color and is configured in a first layer while the peak exposure indicator is configured in a second layer, the second layer being disposed between the cumulative exposure indicator and the substrate and the peak exposure indicator being viewable through the cumulative exposure indicator when transparent. Further, optionally, in the example embodiment of the dual-function heat indicator the cumulative exposure indicator may be configured in one layer and the peak exposure indicator may be disposed in the same layer as the cumulative exposure indicator.

Optionally in the example embodiment of the dual-function heat indicator the substrate may be configured to be conformable with a host product which may enable the dual-function heat indicator to be attachable to the host product, optionally, by bearing a pressure-sensitive adhesive layer. Further, optionally, in the example embodiment of the dual-function heat indicator the first reactant and the second reactant may be solid and the meltable solid may further include a thermal sensitizer to modify the melting point of the peak meltable solid. Further, the meltable solid may include a binder. Alternatively, in the example embodiment of the dual-function heat indicator the first reactant may include a color former and the second reactant may include a color developer and wherein, optionally, the color former or the color developer, or both the color former and the color developer, are initially colorless.

Optionally, in the example embodiment of the dual function heat indicator the color developer may be chosen from a group consisting of an oil-soluble reducing agent, oxalic acid, phosphite ester, hydroxybenzoic acid ester, hydrohydroquinone, a hydroquinone derivative such as dimethyhydroquinone, di-tert-butyl hydro quinone, dialkylhydroquinone, 3-ethoxyphenol, 1,2-diethyl-3-hydroxybenzene,1,3-diethyl-2-hydroxybenzene, 2,2'-methylenebis(3,4,6 trichlorophenol); meltable, or sensitizer-soluble, primary and secondary amines having low water solubility, for example, 4-butyl-aniline, phenol derivatives, organic acids, acid clays, reactive acid hectorite clay, phenolic resins, phenol-acetylene resins, polyvalent metallic salts of phenolic resins, zinc-including modified alkyl phenolic resin, zinc salicylate, zinc salicylate resin, 4,4'-isopropylidenebisphenol (also known as bisphenol A), 1,7-di(hydroxyphenylthio)-3,5-dioxaheptane, 4-hydroxyethyl benzoate, 4-hydroxydimethyl phthalate, monobenzyl phthalate, bis-(4-hydroxy-2-methyl-5-ethylphenyl)sulfide, 4-hydroxy-4'-isopropoxydiphenylsulfone, 4-hydroxyphenylbenzenesulfonate, 4-hydroxybenzoyloxybenzylbenzoate, bis-(3-1-butyl-4-hydroxy-6-methylphenyl) sulfone, p-tert-butylphenol, or polymers based on bisphenol A.

Further, alternatively, in the example embodiment of the dual function heat indicator the color former may be chosen from a group including 3,3-bis(p-dimethylaminophenyl)-phthalide, 3,3-bis(p-dimethylaminophenyl)-6-dimethylaminophthalide (crystal violet lactone), 3,3-bis(p-dimethylaminophenyl)-6-diethylaminophthalide, 3,3-bis(p-dimethylaminophenyl)-6-chlorophthalide, 3,3-bis(p-dibutylaminophenyl)-phthalide, 3-(N—N-diethylamino)-5-methyl-7-(N,N-dibenzylamino) fluoran, 3-dimethylamino-5,7-dimethylfluoran, 3-diethylamino-7-methylfluoran, 3-(2'-hydroxy-4'-dimethylaminophenyl)-3-(2'-methoxy-5'-chlorophenyl)phthalide, 3-(2'-hydroxy-4'-dimethylaminophenyl)-3-(2'-methoxy-5'-nitrophenyl-phthalide, 3-(2'-hydroxy-4'-diethylaminophenyl)-3-(2'-methoxy-5'-methylphenyl)phthalide, 3-(2'-methoxy-4'-dimethylaminophenyl)-3-(2'-hydroxy-4'-chloro-5'-methylphenyl)-phthalide, benzoylleuco methylene blue, malachite green lactone, N-2,4,5-trichlorophenylleuco auramine, 3-diethylamino-6-methyl-7-chlorofluoran, 3,6-bis (diethylamino)fluoran-γ-(4'-nitro)-anilinolactam, 3-diethyl-amino-6-methyl-7-anilinofluoran, 3-(N-ethyl-N-isoamy-lamino)-6-methyl-7-anilinofluoran, 3-cyclohexylamino-6-chlorofluoran or 3-diethylamino-6,8-dimethylfluoran.

Further in the example embodiment of the dual-function heat indicator the cumulative exposure indicator may include at least one thermally sensitive, polymerizable diacetylenic compound containing at least two conjugated acetylenic groups. Furthermore, the cumulative heat exposure color change may be irreversible and occur after a predetermined cumulative heat exposure. Optionally the example embodiment of the dual-function heat indicator may include a freeze indicator wherein the freeze indicator is supported by the substrate and wherein, optionally, the freeze indicator may be transparent before activation by exposure to a freezing temperature, may be supported on the cumulative exposure indicator and the cumulative exposure indicator or may be viewable through the freeze indicator.

Optionally in the example embodiment of the dual function heat indicator the substrate may include a printed reference surface. The substrate may be a synthetic sheet or film further comprised of polyethylene, polypropylene, polycarbonate, polyester, polyamide, polyurethane, polyvinyl chloride, polyvinylidene chloride, cellulose-derived materials, aluminum foil, paper, or coated paper. Alternatively, substrate may be clear or white. Optionally in the example embodiment the substrate may be a clear polyester film. In the example embodiment of the dual function heat indicator the peak indicator may include a pre-manufactured thermal paper or film having a normal color change activation temperature of greater than 60° C.

The example embodiment of the dual function heat indicator may include an activator applied to the pre-manufactured thermal paper or film configured to lower the color change activation temperature of the pre-manufactured thermal paper or film to below 60° C. Optionally, the activator may be an organic solvent chosen from a group consisting of heptadecanol, 4-methoxyphenol, pentadecanol, 2,4-di-tert-butyl phenol or benzophenone.

Alternatively in the example embodiment of the dual function indicator the activator may be chosen to have a melting point that is approximately the same as a desired predetermined peak ambient temperature threshold that is indicated by the peak exposure indicator. The example embodiment of the dual function heat indicator may further optionally include a barrier separating the activator from the pre-manufactured thermal paper or film, the barrier configured to allow the activator to contact the thermal paper in response to an ambient heat exposure peak temperature greater than a predetermined peak temperature, but less than the normal activation temperature of the thermal paper. Further, the barrier may be a meltable solid.

Optionally, in the example embodiment of the dual-function heat indicator the peak exposure indicator may have a response temperature chosen from the group consisting of in the range from about 30° C. to about 50° C., in the range of from about 40° C. to about 60° C., in the range of from about 30° C. to about 40° C., in the range of from about 40° C. to about 50° C., in the range of from about 50° C. to about 60° C., in the range of from about 30° C. to about 35° C., in the range of from about 35° C. to about 40° C., in the range of from about 40° C. to about 45° C., in the range of from about 45° C. to about 50° C., in the range of from about 50° C. to about 55° C., in the range of from about 55° C. to about 60° C., about 30° C., about 35° C., about 40° C., about 45° C., about 50° C., about 55° C., of and about 60° C.

In another example embodiment of the dual-function heat indicator for monitoring cumulative ambient heat exposure and peak ambient heat exposure, the dual-function heat indicator includes a substrate, a cumulative exposure indicator supported by the substrate in one viewable layer of the dual-function heat indicator, the cumulative exposure indicator being color-changeable in response to cumulative ambient heat exposure, and a peak exposure indicator supported by the substrate in another viewable, layer of the dual-function heat indicator, the peak exposure indicator comprising a meltable particulate colored material, wherein the meltable particulate colored material has an average particle size imbuing the meltable particulate colored material with a light color, the light color being attributable to scattering of visible light by the meltable colored material particles, wherein melting of the meltable particulate colored material causes the peak exposure indicator to change its visual appearance, the change in appearance being induced by an ambient heat exposure peak reaching a temperature exceeding the melting point of the meltable particulate colored material, and wherein the dual-function heat indicator indicates cumulative ambient heat exposure or peak ambient heat exposure by changing color.

Optionally in the example embodiment of the dual heat indicator the change in appearance of the peak exposure indicator may be caused by the meltable particulate colored material darkening in color or may be caused by the melting of the meltable particulate material revealing a background or may be caused by the melting of the meltable particulate material obscuring a background. Alternatively, in the example embodiment of the dual-function heat indicator the meltable particulate colored material includes a meltable solid and a dye dissolved in the meltable solid.

In yet another example embodiment, a heat event indicator for monitoring ambient heat exposure to a temperature traversing a threshold temperature includes a substrate and a coalesceable particulate colored material supported by the substrate wherein the coalesceable particulate colored material has an average particle size imbuing the coalesceable particulate colored material with a light color, the light color being attributable to scattering of visible light by the coalesceable colored material particles wherein coalescence of the coalesceable particulate colored material causes the coalesceable particulate colored material to darken in color, the darkening being induced by an ambient heat exposure event reaching a temperature traversing the threshold temperature and wherein the heat event indicator indicates the occurrence of the ambient heat exposure event by changing color. Alternatively in this example embodiment of the heat event indicator the threshold temperature may be a peak temperature and the coalesceable particulate colored material may be meltable and melts in response to the ambient heat exposure event. Optionally, in the example embodiment of the heat event indicator the threshold temperature may be a freezing temperature, the heat event indicator including a dispersion of the coalesceable particulate colored material in aqueous liquid medium, wherein the dispersion collapses and the coalesceable particulate colored material coalesces in response to the ambient heat exposure event.

Further in another example embodiment of the dual-function heat indicator or heat event indicator the host product and the dual-function heat indicator or the heat event indicator may be associated to monitor the host product for heat exposure; the host product, optionally, being a medical product comprising a heat-sensitive proteinaceous component.

In yet another example embodiment of the dual function heat indicator a method of making a dual-function heat indicator for monitoring cumulative ambient heat exposure and peak ambient heat exposure, optionally, being a dual-function heat indicator includes applying a liquid composition comprising a cumulative heat-sensing agent to a substrate, the cumulative heat-sensing agent being color-changeable in response to cumulative ambient heat exposure and being transparent prior to changing color, and drying the liquid composition on the substrate to provide a dried composition, without changing the color of the heat-sensing agent, incorporating a peak exposure indicator composition in the liquid composition, the peak exposure indicator composition comprising a first reactant, a second reactant and a meltable solid, or supporting a peak exposure indicator comprising a first reactant, a second reactant and a meltable solid on the substrate prior to the application of the liquid composition and applying the liquid composition over the peak exposure indicator on the substrate wherein the first reactant and the second reactant are chemically co-reactable to provide a color change, the meltable solid physically separates the first reactant from the second reactant in the dried composition or in the substrate-supported peak exposure indicator, and the color-changing chemical reaction is induced in response to an ambient heat exposure peak. Optionally the example embodiment of the method of making the dual heat indicator may include applying the peak exposure indicator composition to a discrete area of the substrate prior to applying the liquid composition and applying the liquid composition to the entire area of the peak exposure indicator. Alternatively, the example embodiment of the method of making the dual heat indicatior may include the substrate bearing a coating of the peak exposure indicator composition, the coating optionally extending over the entire area of the substrate. Optionally, in the example embodiment of the method of making the dual heat indicator the first reactant and second reactant are both particulate and the liquid composition includes an aqueous dispersion of the first reactant, the second reactant and the meltable solid.

In yet another example embodiment, the method for treating a thermal substrate configured to respond to an ambient temperature above a first predetermined threshold by changing color, the method includes applying an activator to the thermal substrate, the activator configured to cause the thermal substrate to change color at an ambient temperature above a second predetermined threshold, the second predetermined threshold substantially lower than the first predetermined threshold. Optionally, in the example embodiment the method may include coating a printable surface of the thermal substrate with the activator wherein the activator includes a meltable solid. Alternatively, in the example embodiment of the method the thermal substrate may include a thermal coating further including a first reactant and a second reactant which are chemically co-reactable to provide a color change, wherein the color change is a chemical reaction being induced in response to a peak temperature exceeding the melting point of the activator. Optionally, in the example embodiment of the method the first reactant may include a color former and the second reactant comprises a color developer and wherein optionally, the color former or the color developer, or both the color former and the color developer are initially colorless. The color developer may be chosen from a group including an oil-soluble reducing agent, oxalic acid, phosphite ester, hydroxybenzoic acid ester, hydrohydroquinone, a hydroquinone derivative such as dimethyhydroquinone, di-tert-butyl hydro quinone, dialkylhydroquinone, 3-ethoxyphenol, 1,2-diethyl-3-hydroxybenzene, 1,3-diethyl-2-hydroxybenzene, 2,2'-methylenebis(3,4,6 trichlorophenol); meltable, or sensitizer-soluble, primary and secondary amines having low water solubility, for example, 4-butylaniline, phenol derivatives, organic acids, acid clays, reactive acid hectorite clay, phenolic resins, phenol-acetylene resins, polyvalent metallic salts of phenolic resins, zinc-including modified alkyl phenolic resin, zinc salicylate, zinc salicylate resin, 4,4'-isopropylidenebisphenol (also known as bisphenol A), 1,7-di(hydroxyphenylthio)-3,5-dioxaheptane, 4-hydroxyethyl benzoate, 4-hydroxydimethyl phthalate, monobenzyl phthalate, bis-(4-hydroxy-2-methyl-5-ethylphenyl)sulfide, 4-hydroxy-4'-isopropoxydiphenylsulfone, 4-hydroxyphenylbenzenesulfonate, 4-hydroxybenzoyloxybenzylbenzoate, bis-(3-1-butyl-4-hydroxy-6-methylphenyl) sulfone, p-tert-butylphenol, or polymers based on bisphenol A. The color former may be chosen from a group including 3,3-bis(p-dimethylaminophenyl)-phthalide, 3,3-bis(p-dimethylaminophenyl)-6-dimethylaminophthalide (crystal violet lactone), 3,3-bis(p-dimethylaminophenyl)-6-diethylaminophthalide, 3,3-bis(p-dimethylaminophenyl)-6-chlorophthalide, 3,3-bis(p-dibutylaminophenyl)-phthalide, 3-(N—N-diethylamino)-5-methyl-7-(N,N-dibenzylamino) fluoran, 3-dimethylamino-5,7-dimethylfluoran, 3-diethylamino-7-methylfluoran, 3-(2'-hydroxy-4'-dimethylaminophenyl)-3-(2'[-methoxy-5'-chlorophenyl)phthalide, 3-(2'-hydroxy-4'-dimethylaminophenyl)-3-(2'-methoxy-5'-nitrophenyl-phthalide, 3-(2'-hydroxy-4'-diethylaminophenyl)-3-(2'-methoxy-5'-methylphenyl) phthalide, 3-(2'-methoxy-4'-dimethylaminophenyl)-3-(2'-hydroxy-4'-chloro-5'-methylphenyl)-phthalide, benzoylleuco methylene blue, malachite green lactone, N-2,4,5-trichlorophenylleuco auramine, 3-diethylamino-6-methyl-7-chlorofluoran, 3,6-bis(diethylamino)fluoran-γ-(4'-nitro)-anilinolactam, 3-diethylamino-6-methyl-7-anilinofluoran, 3-(N-ethyl-N-isoamylamino)-6-methyl-7-anilinofluoran, 3-cyclohexylamino-6-chlorofluoran or 3-diethylamino-6,8-dimethylfluoran. Optionally, in the example embodiment of the method it may further include barrier which prevents direct contact between the activator and the thermal coating and wherein the barrier is a meltable solid with a melting point of about the second threshold temperature, wherein an ambient temperature above the second predetermined threshold causes melting of the barrier triggering the reaction between the first reactant and second reactant to chemically co-react and provide a color change. Optionally in the example embodiment of the method the meltable solid is chosen to have a melting point that is approximately the same as a desired predetermined peak ambient temperature threshold that is indicated by the peak exposure indicator. Alternatively in the example embodiment of the method the thermal substrate may be pre-manufactured thermal paper or pre-manufactured thermal film. Optionally, in the example embodiment of the method the activator may be an organic solvent, preferably chosen from a group including heptadecanol, 4-methoxyphenol, pentadecanol, 2,4-di-tert-butyl phenol or benzophenone, and more preferably the activator is benzophenone. Alternatively in the example embodiment of the method the ambient temperature above the second predetermined threshold may cause melting of the activator triggering the reaction between the first reactant and second reactant to chemically co-react and provide a color change.

In yet a further example embodiment a peak heat indicator includes a pre-manufactured thermal substrate normally configured to respond to an ambient temperature above a first predetermined threshold by changing color, and an activator applied to the thermal substrate and configured to interact with the pre-manufactured thermal substrate so that the pre-manufactured substrate changes color to respond to an ambient temperature above a second predetermined threshold by changing color, the second predetermined threshold being substantially lower than the first predetermined threshold. Optionally in the example embodiment of the peak heat indicator the activator may include a meltable solid having a melting point approximately the same as the second predetermined temperature, wherein an ambient temperature above the second predetermined threshold causes melting of the activator triggering the reaction between the first reactant and second reactant, causing them to chemically co-react and provide a color change. Alternatively in the example embodiment of the peak indicator the meltable solid may be chosen to have a melting point that is approximately the same as a desired predetermined peak ambient temperature threshold that is indicated by the peak exposure indicator. Optionally in the example embodiment of the peak indicator the thermal substrate may include a thermal coating further include a first reactant and a second reactant which are chemically co-reactable to provide a color change wherein the color, change is a chemical reaction being induced in response to a peak temperature exceeding the melting point of the activator. Alternatively in the example embodiment of the peak indicator the first reactant comprises a color former and the second reactant comprises a color developer and wherein optionally, the color former or the color developer, or both the color former and the color developer are initially colorless. Optionally in the example embodiment of the peak indicator the color developer may be chosen from a group including an oil-soluble reducing agent, oxalic acid, phosphite ester, hydroxybenzoic acid ester, hydrohydroquinone, a hydroquinone derivative such as dimethyhydroquinone, di-tert-butyl hydro quinone, dialkylhydroquinone, 3-ethoxyphenol, 1,2-diethyl-3-hydroxybenzene, 1,3-diethyl-2-hydroxybenzene, 2,2'-methylenebis(3,4,6 trichlorophenol); meltable, or sensitizer-soluble, primary and secondary amines having low water solubility, for example, 4-butyl-aniline, phenol derivatives, organic acids, acid clays, reactive acid hectorite clay, phenolic resins, phenol-acetylene resins, polyvalent metallic salts of phenolic resins, zinc-including modified alkyl phenolic resin, zinc salicylate, zinc salicylate resin, 4,4'-isopropylidenebisphenol (also known as bisphenol A), 1,7-di(hydroxyphenylthio)-3,5-dioxaheptane, 4-hydroxyethyl benzoate, 4-hydroxydimethyl phthalate, monobenzyl phthalate, bis-(4-hydroxy-2-methyl-5-ethylphenyl)sulfide, 4-hydroxy-4'-isopropoxydiphenylsulfone, 4-hydroxyphenylbenzenesulfonate, 4-hydroxybenzoyloxybenzylbenzoate, bis-(3-1-butyl-4-hydroxy-6-methylphenyl)sulfone, p-tert-butylphenol, or polymers based on bisphenol A.

Optionally in the example embodiment of the peak indicator the color former is chosen from a group consisting of: 3,3-bis(p-dimethylaminophenyl)-phthalide, 3,3-bis(p-dimethylaminophenyl)-6-dimethylaminophthalide (crystal violet lactone), 3,3-bis(p-dimethylaminophenyl)-6-diethylaminophthalide, 3,3-bis(p-dimethylaminophenyl)-6-chlorophthalide, 3,3-bis(p-dibutylaminophenyl)-phthalide, 3-(N—N-diethylamino)-5-methyl-7-(N,N-dibenzylamino) fluoran, 3-dimethylamino-5,7-dimethylfluoran, 3-diethylamino-7-methylfluoran, 3-(2'-hydroxy-4'-dimethylaminophenyl)-3-(2'[-methoxy-5'-chlorophenyl)phthalide, 3-(2'-hydroxy-4'-dimethylaminophenyl)-3-(2'-methoxy-5'-nitrophenyl-phthalide, 3-(2'-hydroxy-4'-diethylaminophenyl)-3-(2'-methoxy-5'-methylphenyl) phthalide, 3-(2'-methoxy-4'-dimethylaminophenyl)-3-(2'-hydroxy-4'-chloro-5'-methylphenyl)-phthalide, benzoylleuco methylene blue, malachite green lactone, N-2,4,5-trichlorophenylleuco auramine, 3-diethylamino-6-methyl-7-chlorofluoran, 3,6-bis(diethylamino)fluoran-γ-(4'-nitro)-anilinolactam, 3-diethylamino-6-methyl-7- anilinofluoran, 3-(N-ethyl-N-isoamylamino)-6-methyl-7-anilinofluoran, 3-cyclohexylamino-6-chlorofluoran or 3-diethylamino-6,8-dimethylfluoran. Alternatively in the example embodiment of the peak indicator the peak heat indication may further include a barrier configured to prevent direct contact between the activator and the thermal coating wherein the barrier is a meltable solid. Optionally in the example embodiment of the peak indicator the thermal substrate is pre-manufactured thermal paper or pre-manufactured thermal film. Alternatively in the example embodiment of the peak indicator the activator is an organic solvent, preferably chosen from a group including heptadecanol, 4-methoxyphenol, pentadecanol, 2,4-di-tert-butyl phenol or benzophenone, and more preferably benzophenone.

BRIEF DESCRIPTION OF THE FIGURES

Some example apparatus embodiments of the invention, and example procedures for making and using one or more example embodiments, are described in detail herein and by way of example, with reference to the accompanying drawings (which are not necessarily drawn to scale with regard to any internal or external structures shown) and in which like reference characters designate like elements throughout the several views, and in which:

FIG. 10 is a table, as it pertains to Example 1 herein, showing the optical density measurements of the active region in the cumulative indicator only, the dual indicator, and the thermal paper construction only, at 90° C. during various time intervals.

FIG. 11 is a table, as it pertains to Example 1 herein, showing the optical density measurements of the active region in the cumulative indicator only, the dual indicator, and the thermal paper construction only, at 80° C. during various time intervals.

FIG. 12 is a table, as it pertains to Example 1 herein, showing the optical density measurements of the active region in the cumulative indicator only, the dual indicator, and the thermal paper construction only, at 50° C. during various time intervals.

FIG. 13 is a table, as it pertains to Example 1 herein, showing the optical density measurements of the active region in the cumulative indicator only, the dual indicator, and the thermal paper construction only, at 37° C. during various time intervals.

FIG. 14 is a table, as it pertains to Example 2 herein, showing the optical density measurements of the active region in the cumulative indicator (similar to HEATmarker VVM14), the dual heat indicator, and the peak indicator (DEGmarker 40), between 25-45° C.

FIG. 15 shows the test cards, as they pertain to Example 2 herein, showing the appearance of the cumulative indicator (similar to HEATmarker VVM14), the dual heat indicator, and the peak indicator (DEGmarker 40) at no heat and heated to 45° C.

FIG. 16 is a table, as it pertains to Example 2, showing the color appearance of the active region in comparison between the dual heat indicator (VVM14-equivalent with DEGmarker 40) and dual heat indicator (VVM14-equivalent with DEGmarker 45).

FIG. 17 is a table, as it pertains to Example 4, listing the sample, vendor, product, type, initial static sensitivity, and appearance of the active region of the samples after 40 min at 43° C.

DETAILED DESCRIPTION

Figure 1:
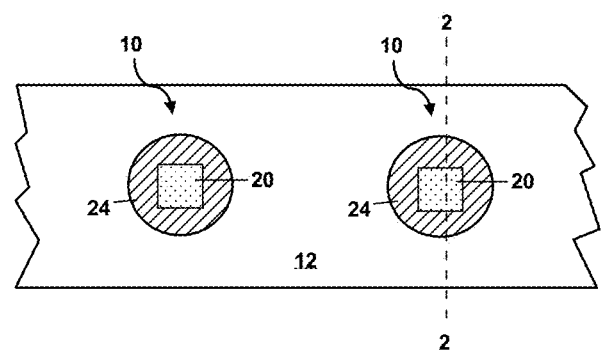
FIG. 1 is a plan view of two example dual-function heat-indicators, according to an example embodiment of the invention, arranged side-by-side on a support liner.

Vaccines are a cost-effective health intervention that may save millions of lives globally. However, difficulties may occur in protecting vaccine supplies from temperature excesses during storage and distribution, particularly, but not exclusively, in low and middle income countries in hot climatic regions. Unless a monitoring device is employed, a medical technician in the field, wishing to administer a vaccine, has no way of distinguishing between vials containing still-potent vaccine dosages from those that may have lost potency due to heat exposure.

The proteins that are usually the active constituents of vaccines are complex molecules that may have sophisticated three-dimensional conformations, the presence of which is essential to elicit an effective immunological response in a human subject to whom a vaccine is administered. Upon heating, proteins generally denature and quickly lose their three-dimensional conformation. Denaturation of a small portion of a vaccine dosage may be enough to compromise the potency of the dosage. Denaturation may occur slowly, as a result of a gradual accumulation of low-level heat exposure, or quickly, as a result of a peak of more intense heat exposure. Similar considerations may apply to other immunogenic molecules, and complex biologicals, whether natural or synthetic.

Cumulative time-temperature indicators have often been applied to vaccine vials to monitor historical cumulative heat exposures experienced by the vaccine and provide a medical technician, or other user, a warning signal that the vaccine has experienced heat exposure that may have affected its freshness or potency. As noted previously herein, a cumulative time-temperature indicator may not respond effectively to a heat exposure peak of relatively brief duration that may also affect freshness or potency.

Thus, a dual-function heat indicator that may signal cumulative ambient heat exposure and peak ambient heat exposure in a single device would be useful to monitor the heat exposure of heat-sensitive products such as a vaccine, and for other purposes. Small low-cost indicators additionally would be desirable for application to typical single-dosage vaccine vials that may have a capacity as small as 5 mL, and a cost, in bulk, that may be below U.S. $0.25 per dosage in 2012, in some cases.

The term "dual," as used herein, refers to at least two and may include more than two. The term "color" as used herein includes achromatic visual appearances such as black, gray, and white, as well as chromatic appearances having primary color hues, secondary color hues and/or other color hues, such as, without limitation, red, yellow, green, blue, purple, orange, brown and other hues. The terms "color change" and its grammatical variants are used to refer to changes in hue, intensity or lightness (or darkness) or other changes in visual appearance.

The time-temperature indicator device described in Prusik et al. '434 may be used to signal actual rather than an apparent end of a product life see e.g. abstract of Prusik et al. '434. The time-temperature indicator device may employ a diacetylenic monomer-including composition or another known time-temperature indicator, as a primary indicator of long term storage of the product. See, e.g., column 4, lines 23-238 of Prusik et al. '434. As described, the primary indicator is assisted in color development by a secondary indicator that triggers, for example, melts, at a predetermined temperature range. At temperatures above the melting point, the material becomes mobile and will diffuse through the layers and add color to the indicator. See, e.g., column 6, lines 26-29 of Prusik et al. '434. As the predetermined temperature range is reached, or exceeded, it initiates a color forming change as a result of the dissolving of a dye composition. See, e.g., column 6, lines 40-55 of Prusik et al. '434. Three working examples described in Prusik et al. '434, Examples I-III, also each employ a meltable material and a dye that apparently dissolves into the meltable material when molten.

According to Prusik et al. '434, the secondary indicia provided by the secondary indicator of the time-temperature indicator as described may be made to change rapidly. Such a system could be used, apparently, to detect the thawing of a frozen product, or the melting of a chocolate confectionary, according to Prusik et al. '434. See, e.g., column 4, lines 50-52.

The diffusion of a meltable material, and dissolution of a dye, although apparently occurring rapidly in relation to the thawing of a frozen food product, or the melting of chocolate, may be unduly time-consuming when the potential denaturation of a protein needs to be monitored in order to indicate the probable condition of a vaccine or a comparable product.

Similar considerations may apply to vaccines administered to animals, to other medical products including proteinaceous active components, to comparable biologicals, and to other similarly heat-sensitive products.

Moreover, the diffusion of a meltable material and the dissolution of a dye described in Prusik et al. '434 may require significant ambient heat energy input, which may delay the appearance of a color change after the onset of an excess temperature exposure peak.

Accordingly, there is a need for a dual-function heat indicator that may monitor cumulative ambient heat exposure and a peak ambient heat exposure in a single device and provide a quick response to the onset of a heat exposure peak and a clear signal of possible excess heat exposure. If the peak exposure indicator component of a dual-function heat indicator responds too slowly to a heat exposure peak, an associated vaccine, or other heat-sensitive product, may denature and lose its potency, or otherwise deteriorate before exhibiting a color change.

A dual-function heat indicator according to some example embodiments of the invention may address such needs by employing a meltable solid physically separating a first reactant from a second reactant wherein the first reactant is co-reactable with the second reactant to provide a color change, and the color-changing chemical reaction is induced in response to an ambient heat exposure peak. The color-changing chemical reaction induced by the melting of the meltable solid, as it responds to a heat exposure peak reaching a temperature exceeding the melting point of the meltable solid, may proceed quickly, providing a prompt color change. A temperature above which such a peak exposure indicator will respond may be predetermined by suitable selection of the component or components of the meltable solid, and the resultant melting point of the meltable solid, and/or the glass transition temperature of the meltable solid, if the latter is relevant. The meltable solid component, or components, may, in some cases, include either or both of the first reactant and the second reactant.

A prompt color change, such as a darkening to a distinct dark end point, may help assure that heat exposure peaks that are potentially damaging to an intended host product, for example, a vaccine, will be properly indicated, for example, by the dark end point, and reduce the risk that a heat exposure peak may have sufficient heat energy to be damaging to the host product, for example, by denaturing a vaccine's proteins, yet will fail to trigger the cumulative exposure indicator.

A peak exposure indicator component of a dual-function heat indicator example embodiment of the invention may be correlated with, or calibrated to, a host product that the dual-function heat indicator is intended to monitor by selection of materials to configure the melting point of the peak exposure indicator to not be higher than a threshold temperature or temperatures in excess which may be harmful to the host product. An example of a threshold temperature is a temperature in the range of from about 40° C. to about 60° C., which may be suitable for monitoring a vaccine or another host product including an active protein or other sensitive biological material or the like. Other threshold temperatures may also be employed, for example, a threshold temperature in the range of from about 20° C. to about 70° C., for these or other applications.

The cumulative exposure indicator component of a dual-function heat indicator example embodiment of the of the invention may be correlated with the heat response characteristics of an intended host product, to track continuous and/or sporadic lower level exposures to which an associated host product may be subject. The cumulative exposure indicator may also provide a distinct color change, for example, a darkening to a dark end point, at a suitable predetermined cumulative heat value, to indicate the probable condition of the host product. In some example embodiments of the of the invention, the cumulative exposure indicator may have a dark end point that is similar to the dark end point of the peak exposure indicator, if the latter indicator has a dark end point. In such example embodiments, the appearances of the two indicators may be visually combined in a single area to provide an integrated signal that may report two partial heat exposures as potentially representing an adverse heat exposure, in combination. Cumulative exposure indicators, as described herein, are sometimes known as time-temperature indicators.

The predetermined cumulative heat value may be selected in various ways, as known in the art, for example, to correspond with a probable imminent loss of efficacy or quality of the host product. The cumulative exposure indicator may be configured to provide a desired end point by appropriate selection of a heat-sensing agent to include in the cumulative exposure indicator, as is known in the art, or in another suitable manner.

Further, a cumulative exposure indicator employed in an example embodiment of the dual-function heat indicator may have a colorless or lightly colored appearance initially, i.e., before activation by heat. In some example embodiments of the invention, the appearance of the cumulative exposure indicator may be transparent or translucent, at least initially, so that the appearance of the peak exposure indicator may be viewed or optically read through the cumulative exposure indicator. Thus, the initial appearance of the cumulative exposure indicator may be largely that of the substrate supporting the cumulative exposure indicator, for example, white. As the cumulative exposure indicator is subjected to thermal exposure, the active surface becomes progressively darker. However, the cumulative exposure indicator may retain some transparency, possibly until the end point of the cumulative exposure indicator is reached.

The term "transparent" is used herein to include "translucent" and to refer to a material which may transmit some or all of the incident light, so that bodies, for example, colored surfaces, beyond the material are visible, yet which may diffuse, scatter, or block some of the incident, light to a limited extent.

The cumulative heat indicator may employ a heat-sensing agent that provides the described initially transparent and subsequent darkening appearances. In some example embodiments of the invention, the heat-sensing agent may be present in particulate form, in admixture with particles of peak exposure indicator composition. In such example embodiments, both the heat-sensing agent and the peak exposure indicator may contribute to the admixture an initially transparent appearance and a darkening appearance subsequent to heat exposure.

Unless the context indicates otherwise, particulate materials employed in dual-function heat indicator example embodiments of the invention, or in example embodiments of the method, may have various particle sizes, as will be known or apparent to a person of ordinary skill in the art, in light of this disclosure. For example, such particulate materials may have an average particle size of not more than about 10 µm, or from about 0.5 µm to about 5 µm. Some aspects of the example embodiments of the invention employ materials that scatter light and may have different average particle sizes.

The color change exhibited by the peak exposure indicator may be irreversible and may occur after a predetermined ambient heat exposure peak has occurred. The response of the peak exposure indicator may be further enhanced, for example, made quicker, by employing particulate first and second reactants and dispersing the first and second reactant particles in the same layer of an example embodiment of the dual-function heat indicator. The meltable solid may partially or completely envelop the particles of the first reactant or the particles of the second reactant or both types of particles, to provide physical separation between the two types of particles and prevent them from reacting prematurely. The particles of the first reactant may be intimately admixed with the particles of the second reactant and physically separated from by a thin layer of the meltable solid. Water insolubility of the first reactant, the second reactant and/or the meltable material may be useful for manufacturing or other purposes.

Further, one or both of the first reactant and the second reactant may be soluble in the meltable solid. Still further, one of the first reactant and the second reactant may be dissolved in, or blended with, the solid material. Yet further, the meltable material may be a first meltable material and a second meltable material and may partially or completely envelop a solution of the first reactant or of the second reactant in the first meltable material. One or more of these measures may be employed to enhance the response of the peak exposure indicator, or for other purposes. For example, such measures may enable the peak exposure indicator to respond quickly after activation by an ambient heat exposure peak, with little, if any, delay for diffusion of an active material or materials.

In some examples embodiments of dual-function heat indicators according to the example embodiment of the invention, the first reactant and the second reactant may be solid. The meltable solid may include a thermal sensitizer to modify the melting point of the peak exposure indicator. The meltable solid may include a binder, whether or not the meltable solid includes a thermal sensitizer.

For use with a host product including an active protein, and for other purposes, the peak exposure indicator may have a response temperature in the range of from about 40° C. to about 60° C. For this purpose, the peak exposure indicator may be meltable at a temperature near to, or at, its response temperature or at a lower temperature for example up to 2° C. lower. The melting points, or range of melting points, of the meltable ingredients of the peak exposure indicator may be selected accordingly.

A first reactant employed in an example embodiment of the dual-function heat indicator may be or may include a color former. A second reactant may be or may include a color developer. Optionally, the color former or the color developer, or both the color former and the color developer, may be colorless initially. The color former may develop color as a result of reacting with the color developer.

A cumulative exposure indicator employed in an example embodiment of the dual-function heat indicator may include at least one thermally sensitive, polymerizable diacetylenic compound including at least two conjugated acetylenic groups, for example, a hexadiyn bis(alkylurea) compound.

The color change exhibited by the cumulative exposure indicator may be irreversible and may occur after a predetermined cumulative ambient heat exposure has occurred. The cumulative exposure indicator may employ various heat-sensing agents, for example, various polymerizable diacetylenic compounds, or other heat-sensing agents, to vary the amount of heat exposure that causes a color change.

Dual-function heat indicator example embodiments of the invention may exhibit a distinct color change following activation that provides good contrast with the appearance of the dual-function heat indicator before activation and a clear, irreversible, signal suggesting that adverse heat exposure may have occurred, for example, a significant darkening of the indicator.

The color change may be described in terms of optical density changes. Optical density "OD" as used herein is the log to the base 10 of the inverse of the incident light reflected from a sample. OD may be expressed by the formula $$OD_\lambda = \log_{10}(I_0/I)$$

where I is the intensity of light at a specified wavelength $\lambda$ that is reflected by a sample and $I_0$ is the intensity of the light before it enters the sample, where I is the intensity of light at a specified wavelength $\lambda$ that is reflected by a sample and $I_0$ is the intensity of the light before it enters the sample. Some example embodiments of the dual-function heat indicator may exhibit an optical density difference of 0.4 OD between the before-activation and the after-activation appearances of the indicator, providing a distinct color change and good contrast. Higher optical differences, for example, 0.5 OD or 0.6 OD, or higher, may also be exhibited. Also, some example embodiments of the dual-function heat indicator may exhibit an optical density difference of 0.2 OD or 0.3 OD between the before-activation and the after-activation appearances of the indicator, also providing a distinct color change. The color change may be provided by a change in color of the cumulative exposure indicator or a change in color of the peak exposure indicator or a combination of changes in color of both indicators.

An example embodiment of the dual-function heat indicator may include a viewable active area for viewing the cumulative exposure indicator and/or the peak exposure indicator and may also include a colored reference area adjacent the active area, which reference area may be colored to show an end point appearance of the active area. The end point appearance may be an appearance such as a dark appearance that indicates a probable condition of an associated host product, for example, that the host product has lost efficacy or quality and should not be used.

Dual-function heat indicator example embodiments of the invention may provide an irreversible, essentially permanent, or non-transitory, record of a historical ambient heat exposure event or events.

One or more other indicators, for example a freeze indicator, may be combined with a dual-function heat indicator example embodiment of the invention. The freeze indicator may be supported on a common substrate with the dual-function heat indicator. For example, the freeze indicator may be transparent before activation by exposure to a freezing temperature and may be supported on the dual-function heat indicator, and the dual-function heat indicator may be viewable through the freeze indicator. Such a construction may provide a simple, compact indicator that may integrate responses to three different environmental inputs: freeze, cumulative heat, and a heat peak, into a single signal, for easy comprehension. Suitable freeze indicators and ways of supporting a freeze indicator on a substrate with one or more other ambient condition indicators are described in U.S. Pat. No. 7,490,575 to Taylor et al. Other suitable freeze indicators are described in U.S. Pat. No. 7,891,310 to Taylor et al. and U.S. Pat. No. 8,122,844 to Smith et al.

A substrate employed in an example embodiment of the dual-function heat indicator may be configured to be conformable with a host product, or packaging for a host product, for example a vaccine vial containing a vaccine. The substrate may be flat to conform with a flat surface of the host product (or to a package containing the host product). Alternatively, the substrate may be curved in one dimension, or in two dimensions, to conform with a curved surface of the host product (or of a package containing the host product), for example, the curved surface of a cylindrical vaccine vial. Also, a substrate may enable the dual-function heat indicator to be attachable to a host product, for example, by bearing a pressure-sensitive adhesive layer. Adhesive attachment is one example of different ways in which the dual-function heat indicator may be associated with a host product to monitor the host product for heat exposure. Possible different ways of attachment include, for example, adhering, tying, looping, and stapling, to the host product directly, or to a package containing the host product, or to a package, carton, box or other container containing a number of host product items. Further, a dual-function heat indicator embodied in a label, or tag, may be inserted in a host product package, carton, or other container for one or more host product items.

Some example embodiments of the dual-function heat indicator may employ a thermal paper, i.e., a paper bearing a thermal coating, the paper functioning as a substrate and the thermal coating functioning as a peak exposure indicator. The characteristics of the thermal coating may be selected, or modified, to provide a thermal paper having peak exposure indicator characteristics rendering the thermal paper suitable for use in an example embodiment of the dual-function heat indicator, in cooperation with a cumulative exposure indicator.

An example of a thermal paper that may be employed is a light weight, well-formed, smooth paper having a thermally responsive surface treatment or coating including color-forming reactants. Some examples of suitable color-forming reactants are a leuco dye precursor as a first reactant, and a developer for the leuco dye as a second reactant. The leuco dye precursor and developer may be solid particulates. The color-forming reactants may be incorporated in a matrix that constitutes a meltable solid. The resultant matrix may be applied to a paper sheet, or continuous paper web, or another suitable substrate. For example, the matrix may be dispersed in a liquid medium and the resultant liquid dispersion may be coated on the substrate and dried. Drying may be conducted at a temperature of at least 2° C. below the melting point of the matrix material to avoid melting the matrix material, employing forced convection, low humidity, for example, a relative humidity below about 50% or below about 40%, and/or an extended drying time. Upon melting, the matrix may enable the leuco dye precursor and developer to merge and develop color.

The thermally responsive coating may also include a thermal sensitizer. The thermal sensitizer may have a relatively low melting point such that the melting point of the thermally responsive coating does not exceed a desired threshold temperature for the host product. Also, the thermal sensitizer may be a solvent for one, or both, of the color-forming reactants so that after the thermal sensitizer melts, following exposure to heat, one or both of the color-forming reactants dissolve in the thermal sensitizer. The melting point of the resultant solution of the sensitizer and reactant may be below the melting point of the sensitizer, reducing the response temperature of the peak exposure indicator, in some cases.

Optional additional ingredients of a thermal paper employed in the practice of the example embodiment of the invention include: stabilizers to enhance image durability, referring to the color image generated by heat exposure; fillers or pigments to extend and/or opacify the coating; binders to hold the coating components together and possibly to separate, or help separate, the reactive components; lubricants to help the paper move steadily and smoothly on a printing press or other manufacturing equipment; dispersants; defoamers; viscosity controllers; and/or antistatic agents. One or more of these optional additional ingredients may be employed according to the requirements of a particular application. A thin clear coat, for example, a coat of a polyurethane or another suitable synthetic polymer, may be applied over the thermal coating to add durability and improve writability, if desired.

In one exemplary method of manufacturing a suitable thermal paper, a leuco dye precursor or other color-forming reactant may be mixed with a thermal sensitizer and milled to a suitable particle size. Optionally, the resultant particles may be encapsulated with a meltable capsule material having a suitable melting point, for example, a poly-condensate polymer such as a cross-linked amino-formaldehyde resin, yielding capsules or microcapsules of the color-forming reactant. Separately, a color developer may also be mixed with the thermal sensitizer and may be added to the other coating ingredients, also as a solid at room temperature. The melting points of the thermal sensitizer(s) and the meltable capsule material may be selected according to the intended response temperature of the peak exposure indicator. If greater separation of the color reactants is desired, the color developer may also be encapsulated in the thermal sensitizer. The thermal sensitizer material employed for the color developer, if any, may be the same as that employed for the color-forming reactant, or may be a different, but compatible, thermal sensitizer material.

On exposure to temperatures above a threshold, the capsule material may soften and become permeable. If the thermal sensitizer also has softened, or melted, the color-forming reactants may mix and react to provide a color change. In such example embodiments of the invention, the thermal sensitizer and/or the capsule material may provide a physical separation between the color-forming reactant and the color developer to prevent contact between the two color reactants. Physical separation may usually be maintained so long as the thermal paper is not exposed to temperatures above the threshold temperature, for example, during manufacture of the thermal paper, manufacture of the dual-function heat indicator, storage, shipping, display, and/or use.

Dual-function heat indicator example embodiments of the invention may be manufactured in various ways. One example of a suitable manufacturing method includes preparing a peak exposure indicator composition for incorporation in the dual-function heat indicator. The peak exposure indicator composition may be prepared by mixing a leuco dye precursor that is solid at room temperature with a thermal sensitizer that is also solid at room temperature. The mixed ingredients may be milled and then encapsulated with a suitable meltable capsule material, for example, a poly-condensate polymer such as a cross linked amino-formaldehyde resin. A leuco dye developer may be included in the peak exposure indicator composition by mixing the leuco dye developer with thermal sensitizer material, both materials optionally being solid particulates at room temperature, and adding the developer mixture to the peak exposure indicator composition.

Figure 2:
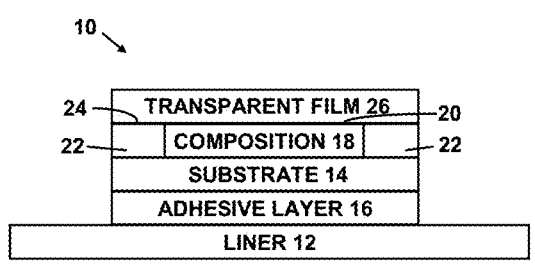
FIG. 2 is a sectional view on the line 2-2 of one example embodiment of one of the example dual-function heat indicators shown in FIG. 1.

Referring now to FIGS. 1 and 2 of the accompanying drawings, the two example embodiments of the dual-function heat indicators shown, referenced 10 in FIGS. 1 and 2, may monitor cumulative ambient heat exposure and a peak ambient heat exposure in a single device. Multiple dual-function heat indicators 10 may be embodied as labels and may be supported on a liner 12 for production in quantity. Various other configurations of dual-function heat indicator 10 are possible. FIG. 1 shows a section of liner 12 on which a number of dual-function heat indicators 10 may be arranged in series, for mass production of the dual-function heat indicators, using print industry technology, or packaging industry technology, or the like. Such label example embodiments may be produced at low cost in self-adhesive configurations and may be suitable for attachment to the outer surface of a mass-produced host product, or to packaging or a container for the host product.

FIG. 2 is a cross-sectional view taken along imaginary line 2-2 in FIG. 1 which demonstrates that dual-function heat indicator 10 may comprise a substrate 14, bearing an adhesive layer 16, which may be pressure sensitive, and which removably adheres substrate 14 to liner 12, so that dual-function heat indicator may be applied to a host product or a package or carton. For this purpose, liner 12 may be a release liner that is coated with a suitable low surface energy material to facilitate removal of adhesive-coated substrate 14. Substrate 14 has a central active region, which bears a color-changing composition 18. Color-changing composition 18 displays an active surface 20 upwardly with respect to substrate 14 for optical reading externally of dual-function heat indicator 10. Active surface 20 displays the added responses of the peak and cumulative components of color changing composition 18. A transparent or opaque reference material 22 may be configured in a ring extending around color-changing composition 18, or in another suitable configuration (not shown) alongside or near color-changing composition 18. Reference material 22 displays a static surface 24 upwardly with respect to substrate 14 for optical reading externally of dual-function heat indicator 10. The appearances of active surface 20 and static surface 24 may be optically read by a human viewer or by a suitable image processing device, for example, a camera.

A transparent film 26 may overlie color-changing composition 18 and reference material 22 to provide protection from physical abrasion or abuse. Transparent film 26 may be secured to color-changing composition 18 and reference material 22 by a layer of adhesive (not shown), or in another suitable manner. Transparent film 26 may bear printed indicia providing identifying or instructional, or other information regarding the dual-function heat indicator and/or an associated host product. Transparent film 26 may be colored to filter out incident ambient light at wavelengths that may adversely affect color-changing composition 18 and may be substantially inert. For example, transparent film 26 may be colored orange or red. Optionally, transparent film 26 may include an ultraviolet filter material to filter, or block incident ultraviolet radiation. Transparent film 26 may be sufficiently transparent that active surface 20 and static surface 24 may be viewed and that the colors, or at least the optical densities at active surface 20 and static surface 24, and changes in the color or optical density at active surface 20 and static surface 24, may be viewed and/or optically read.

Dual-function heat indicator 10, color-changing composition 18, and reference material 22 may have any desired shape. The shapes, considered independently, may be circular, square, rectangular, triangular, hexagonal, polygonal, elongated, circular, oval, elliptical, strip-like, another regular shape, an irregular shape, a shape representing a recognizable image such as a check mark, or another suitable shape. As shown in FIG. 1, by way of example, dual-function heat indicator 10 is circular, reference material 22 occupies a smaller circle, and color-changing composition 18 is configured as a square within the circle of reference material 22.

In the transverse dimension shown in FIG. 2, dual-function heat indicator 10 has a layered structure. The shapes and relative dimensions of the various layers may be varied significantly. One example embodiment of dual-function heat indicator 10 has thin, laminar layers to provide a low-profile device that may have a compact configuration and may be applied to small host products such as vaccine vials and the like.

The size of a dual-function heat indicator such as dual-function heat indicator 10 may vary according to the intended application, or for other purposes. Some example embodiments of such a dual-function heat indicator may have a largest transverse dimension, which may be a dimension in the plane of FIG. 1A, in the range of from about 5 mm to about 30 mm, for example, from about 10 mm to about 15 mm. In such an embodiment, active surface 20 may have a largest transverse dimension of from about 1 mm to about 10 mm, for example, from about 2 mm to about 6 mm.

Color-changing composition 18 may include a heat-sensing agent that functions as a cumulative heat indicator and a peak exposure indicator composition that functions as a peak exposure indicator. Suitable heat-sensing agents and peak exposure indicator compositions are described elsewhere herein. Thus, color-changing composition 18 may change color in response to cumulative heat exposure and may also change color in response to peak heat exposure. In this way, the cumulative exposure indicator and the peak exposure indicator may be integrated into a single layer of dual-function heat indicator 10.

The heat-sensing agent and the peak exposure indicator composition may be configured on substrate 14 so that the appearances of their individual color responses at active surface 20 are mixed additively, i.e. so that any darkening of the cumulative exposure indicator adds to any darkening of the peak exposure indicator to provide a still darker appearance at active surface 20. In terms of optical density, the individual optical densities of the individual appearances are considered. The heat-sensing agent and the peak exposure indicator composition may be configured by admixing or blending particulates in various ways. For example, particles of the heat-sensing agent and particles of the peak exposure indicator composition may be dispersed in a common liquid vehicle, the resultant dispersion may be dispersed on substrate 14, and the liquid vehicle then may be evaporated, or the particulates may be applied to substrate 14 in a radiation-curable coating, which may then be cured with the appropriate radiation.

Reference material 22 may help a viewer or viewing device judge the state of color-changing composition 18 by having an appearance similar to the appearance color-changing composition 18 which will develop after a predetermined cumulative heat exposure indicative of an end point.

Figure 1A:
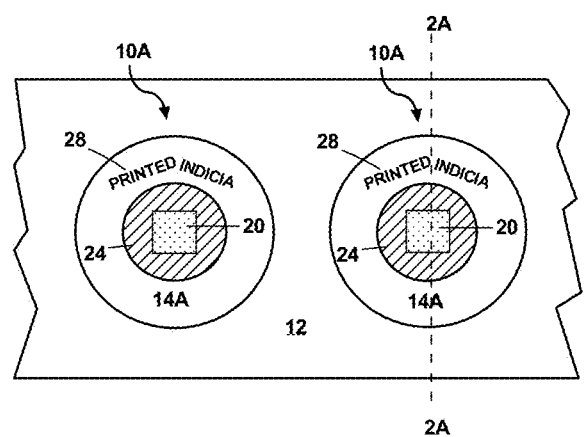
FIG. 1A is a plan view of two dual-function heat-indicators with a printable margin according to the example embodiment of the invention arranged side-by-side on a support liner.
Figure 2A:
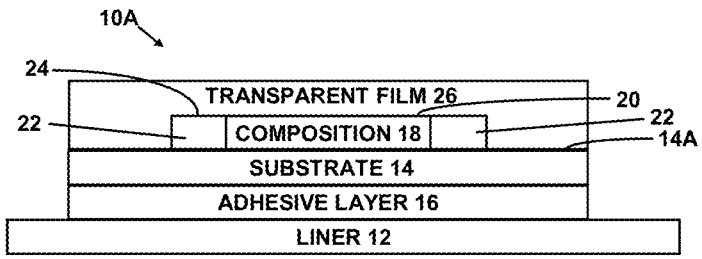
FIG. 2A is a sectional view on the line 2A-2A of one example embodiment of one of the example dual-function heat indicators with a printable margin shown in FIG. 1A.

In another example embodiment as demonstrated in FIG. 1A, dual-function heat indicator 10 may have a substrate 14 with a substrate printable margin 14A on which printed indicia 28 may be printed. FIG. 2A shows a cross sectional view taken along imaginary line 2A-2A in FIG. 1A. FIG. 2A demonstrates that the substrate printable margin 14A surrounds/lies in an outer ring fashion around color changing composition 18 and reference material 22. Otherwise, dual-function heat indicator 10 shown in FIGS. 1A and 2A may be very similar to that in FIGS. 1 and 2, in that the dual-function heat indicator in FIGS. 1A and 2A may also include a liner 12, a substrate 14, an adhesive layer 16, an active surface 20, a reference material 22, a static surface 24, and optionally, a transparent film 26. As such, these components are given the same reference numerals in FIGS. 1A and 2A and are not described further here.

Figure 3:
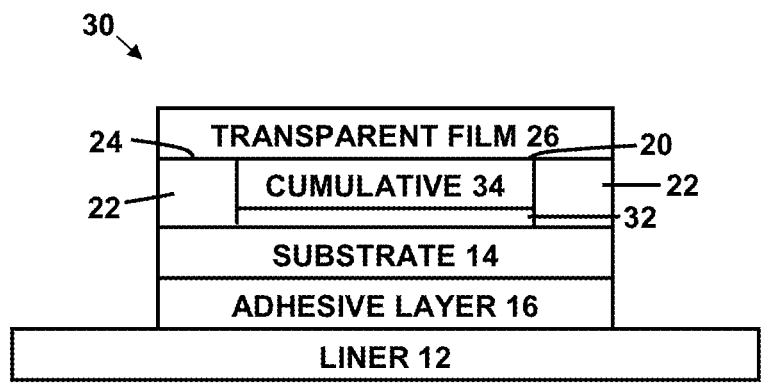
FIG. 3 is a view similar to FIG. 2 of another example embodiment of the example dual-function heat indicator shown in FIG. 1.

Referring to FIG. 3, the dual-function heat indicator shown, referenced 30 in FIG. 3, is generally similar to dual-function heat indicator 10, with the difference that a cumulative exposure indicator and a peak exposure indicator are configured in separate, individual layers rather than being integrated into a single layer of the device, as in dual-function heat indicator 10. The cumulative exposure indicator and peak exposure indicator are prepared and printed separately. In plan view, dual-function heat indicator 30 is similar to dual-function heat indicator 10 so that no additional plan view of dual-function heat indicator 30 is shown.

Like dual-function heat indicator 10, dual-function heat indicator 30 may include a liner 12, a substrate 14, an adhesive layer 16, an active surface 20, a reference material 22, a static surface 24, optionally, a transparent film 26 and, optionally, printed indicia 28 (not shown in the cross-section). Accordingly, these components are given the same reference numerals in FIG. 3 and are not described further here.

Dual-function heat indicator 30 further includes a peak exposure indicator 32 supported on a central region of substrate 14, and a cumulative exposure indicator 34 overlying peak exposure indicator 32. Cumulative exposure indicator 34 may be initially transparent prior to heat exposure so that the appearance of peak exposure indicator 32 is optically readable or viewable through cumulative exposure indicator 34. Thus, dual-function heat indicator 30 combines the appearances of the cumulative exposure indicator and the peak exposure indicator. With this configuration, an end point may be individually indicated by the cumulative exposure indicator, by the peak exposure indicator, or by a combination of a partial exposure of each indicator.

In one example embodiment of the use of dual-function heat indicator 30, in response to a brief exposure to a temperature above a predetermined peak temperature, cumulative exposure indicator 34 remains essentially transparent and lighter in color than reference surface 22. Meanwhile, active surface 20 of combined cumulative explosive indicator 34 and peak exposure indicator 32 darkens rapidly reaching the end point of dual-function heat indicator 30. Darkening occurs as a result of the melting of a wax matrix, or other meltable solid, and the chemical reaction of the dye precursor with the dye developer, or of other color-changing reactants.

Dual-function heat indicator 30 may provide manufacturing or product benefits arising from the separation of the heat-sensing agent employed in cumulative exposure indicator 34 into one layer, if a heat-sensing agent is employed, while the color-forming reactants employed in peak exposure indicator 32 are in another layer.

In a modified example embodiment of dual-function heat indicator 30 (not shown), peak exposure indicator 32 is disposed on top of cumulative exposure indicator 34. In this case, peak exposure indicator 32 may be transparent to permit the appearance of cumulative exposure indicator 34 to be viewed, or read optically, at active surface 20, whereas cumulative exposure indicator 34 may now be either transparent or opaque. Active surface 20 displays the added responses of the peak and cumulative components.

Figure 4:
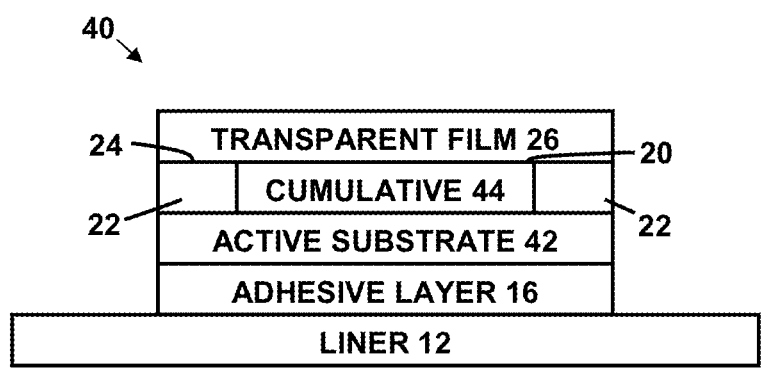
FIG. 4 is a view similar to FIG. 2 of a further example embodiment of the example dual-function heat indicator shown in FIG. 1.

Referring to FIG. 4, the dual-function heat indicator shown, referenced 40 in FIG. 4, is also generally similar to dual-function heat indicator 10. Like dual-function heat indicator 30 in the FIG. 3 example embodiment, dual-function heat indicator 40 differs from dual-function heat indicator 10 by having a cumulative exposure indicator and a peak exposure indicator that are configured in separate individual layers. However, in contrast to the FIG. 3 example, in dual-function heat indicator 40, the peak exposure indicator is integrated into a single layer with a substrate.

Once again, dual-function heat indicator 40 has a similar plan view to that of dual-function heat indicator 10 so that no additional plan view of dual-function heat indicator 40 is shown.

Like dual-function heat indicator 10, dual-function heat indicator 40 may include a liner 12, an adhesive layer 16, an active surface 20, a reference material 22, a static surface 24, optionally, a transparent film 26 and, optionally, printed indicia 28 (not shown in the cross-section). Accordingly, these components are given the same reference numerals in FIG. 4 and are not described further here.

Dual-function heat indicator 40 further includes an active substrate 42 and a cumulative exposure indicator 44 supported on active substrate 42. Active substrate 42 provides substrate functionality similar to that of substrate 14 of dual-function heat indicator 10 and may be fabricated from similar substrate materials, for example, paper or synthetic polymer material. In addition, active substrate 42 includes a peak exposure indicator. The peak exposure indicator may be provided as a deposit of a peak exposure indicator composition, on the upper surface of active substrate 42. This deposit or coating is not referenced separately in FIG. 4. As described in more detail elsewhere herein, the peak exposure indicator composition may include a first reactant and a second reactant. The second reactant may co-react chemically with the first reactant to provide a color change and the peak exposure indicator composition may be meltable to induce the color change. In this example embodiment of the dual-function heat indicator, the peak exposure indicator embodied in active substrate 42 extends beneath reference material 22. Accordingly, reference material 22 may be opaque, and may lack transparency, so that the upper surface of active substrate 42 is not viewable through reference material 22, as this view could be confusing when active substrate 42 darkens as a result of a heat exposure peak.

Cumulative exposure indicator 44 may be similar to cumulative exposure indicator 34 in the FIG. 3 example embodiment of a dual-function heat indicator already described. Thus, cumulative exposure indicator 44 may be transparent initially and the appearance of the peak exposure indicator applied to the upper surface of active substrate 42 may be optically readable or viewable through cumulative exposure indicator 44. Like dual-function heat indicator 30, dual-function heat indicator 40 combines the appearances of the cumulative exposure indicator and the peak exposure indicator. With the configuration of dual-function heat indicator 40 shown in FIG. 4, an end point may also be indicated individually by the cumulative exposure indicator or the peak exposure indicator, or by a combination of a partial exposure of each indicator.

Dual-function heat indicator 40 illustrates an example embodiment of the invention wherein active substrate 42 may be self-supporting prior to assembly into dual-function heat indicator 40 and may be supplied to a point of manufacture from bulk stock such as a sheet, strip or a continuous web of material. This capability may assist the manufacturing process. Also, deposition of the peak exposure indicator composition on suitable substrate material may be performed prior to manufacture of dual-function heat indicator 40, which may simplify the manufacturing process.

In a modified example embodiment of dual-function heat indicator 40 (not shown), active substrate 42 is disposed on top of cumulative exposure indicator 44. In this case, active substrate 42 may be transparent to permit the appearance of cumulative exposure indicator 44 to be viewed, or read optically, at active surface 20, whereas cumulative exposure indicator 44 may be either transparent or opaque. In this modified example embodiment, an inactive substrate layer, like substrate 14 shown in FIGS. 2 and 3, may also be employed between adhesive layer 16 and cumulative exposure indicator 44, as shown in FIG. 4, to provide support.

Figure 5:
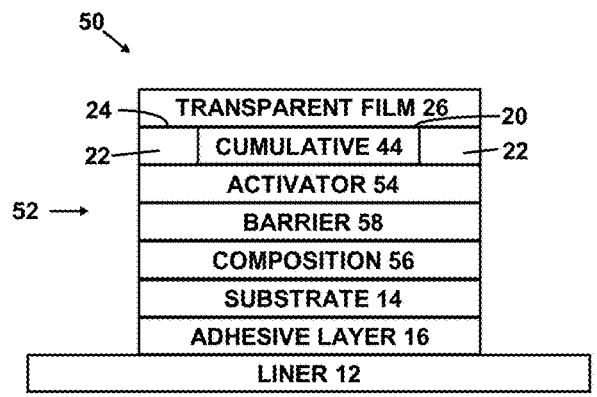
FIG. 5 is a view similar to FIG. 2 of a further example embodiment of the example dual-function heat indicator shown in FIG. 1.

Referring to FIG. 5, the dual-function heat indicator shown, referenced 50 in FIG. 5, is also generally similar to dual-function heat indicator 10. Like dual-function heat indicator 40 in the FIG. 4 example embodiment, dual-function heat indicator 50 differs from dual-function heat indicator 10 by having a cumulative exposure indicator and a peak exposure indicator that are configured in separate individual layers. Cumulative exposure indicator 44 and peak exposure indicator 52 are configured in separate layers. However, in contrast to the FIG. 4 example embodiment, in dual-function heat indicator 50, the peak exposure indicator may include three layers, namely, activator 54, color changing composition 56, and barrier 58. Activator 54 may be a meltable solid which when liquid is a solvent for one or both co-reactants or it may be a reactant. Activators were screened and it was found that meltable activators may be chosen with different effective temperatures so that thermal coatings with normally high thermal response temperatures and temperate dependent color development may be used for a family of peak indicators with a lower activation temperature suitable for the dual indicators in this disclosure. A few activators include, but are not limited to, heptadecanol, 4-methoxyphenol, pentadecanol, 2,4-di-tert-butyl phenol or benzophenone. Various treatments of off-the-shelf commercial or pre-manufactured papers may be used to lower their activation temperature. Color changing composition 56 may include a first reactant and a second reactant, which may co-react chemically to provide a color change. Color changing composition 56 may be layer or coating on substrate 14. Barrier 58 may be a thin clear coating on the surface of color changing composition 56 to prevent direct contact of activator 54 in the solid state with color changing composition 56 and to provide durability.

Like dual-function heat indicator 10, dual-function heat indicator 50 may include a liner 12, a substrate 14, an adhesive layer 16, an active surface 20, a reference material 22, a static surface 24, optionally, a transparent film 26 and, optionally, printed indicia (not shown) as demonstrated in FIG. 5. Accordingly, these components are given the same reference numerals in FIG. 4 and are not described further here.

In a further example embodiment of dual-function heat indicator 50, dual-function heat indicator 50 may omit cumulative exposure indicator 44 so that peak exposure indicator 52 including activator 54, color changing composition 56, and barrier 58 is used as a standalone peak indicator.

Figure 6:
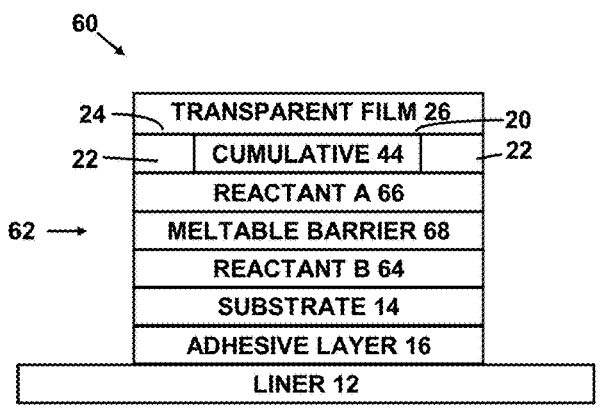
FIG. 6 is a view similar to FIG. 2 of a further example embodiment of the example dual-function heat indicator shown in FIG. 1.

Referring to FIG. 6, the dual-function heat indicator shown, referenced 60 in FIG. 6, is also generally similar to dual-function heat indicator 10. Like dual-function heat indicator 40 in the FIG. 4 example embodiment, dual-function heat indicator 60 differs from dual-function heat indicator 10 by having a cumulative exposure indicator and a peak exposure indicator that are configured in separate individual layers. Cumulative exposure indicator 44 and peak exposure indicator 62 are configured in separate layers. However, in contrast to the FIG. 4 example embodiment, in dual-function heat indicator 60, the peak exposure indicator may include three layers, namely, reactant B 64, reactant A 66, and meltable barrier 68. Reactant B 64 may be a layer including either of the co-reactants described previously, or it may be a coating on substrate 14. Further reactant B 64 may be a mixture including binders. Reactant A 66 may be a layer including the complementary color generating co-reactant for reactant B 64. Further reactant A 66 may be a mixture including binders. Meltable barrier 68 may be a continuous layer of a meltable solid separating reactant A 66 and reactant B 64. Neither reactant A 66 nor reactant B 64 is able to pass through barrier 68 while it is a solid. Once meltable barrier 68 melts into liquid form reactant A 66 and reactant B 64 may co-react chemically to provide a color change.

Like dual-function heat indicator 10, dual-function heat indicator 60 may include a liner 12, a substrate 14, an adhesive layer 16, an active surface 20, a reference material 22, a static surface 24, optionally, a transparent film 26 and, optionally, printed indicia (not shown) as demonstrated in FIG. 6. Accordingly, these components are given the same reference numerals in FIG. 4 and are not described further here.

In a further example embodiment of dual-function heat indicator 60, dual-function heat indicator 60 may omit cumulative exposure indicator 44 so that peak exposure indicator 62 including reactant B 64, reactant A 66, and meltable barrier 68 is used as a standalone peak indicator.

Figure 7:
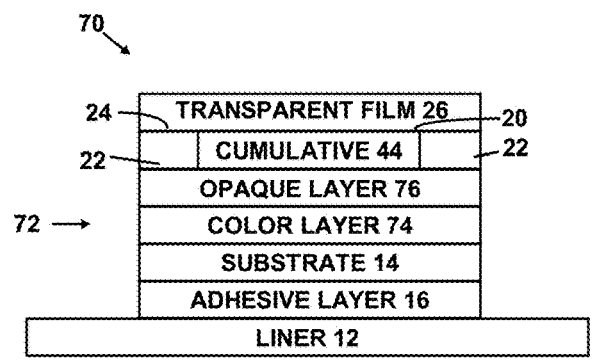
FIG. 7 is a view similar to FIG. 2 of a further example embodiment of the example dual-function heat indicator shown in FIG. 1.

Referring to FIG. 7, the dual-function heat indicator shown, referenced 70 in FIG. 7, is also generally similar to dual-function heat indicator 10. Like dual-function heat indicator 40 in the FIG. 4 example embodiment, dual-function heat indicator 70 differs from dual-function heat indicator 10 by having a cumulative exposure indicator and a peak exposure indicator that are configured in separate individual layers. Cumulative exposure indicator 44 and peak exposure indicator 72 are configured in separate layers. However, in contrast to the FIG. 4 example embodiment, in dual-function heat indicator 70, the peak exposure indicator may include two layers, namely, color layer 74 and opaque layer 76. Color layer 74 may have an intense color such as black or red and may be configured as a layer on top of substrate 14. Opaque layer 76 may be a meltable solid applied as a coating or ink onto color layer 74 or may be small particles that scatter light rendering the layer opaque. Upon melting opaque layer 76 becomes transparent and color layer 74 may be seen through it. Opaque layer 76 may be a wax.

Like dual-function heat indicator 10, dual-function heat indicator 70 may include a liner 12, a substrate 14, an adhesive layer 16, an active surface 20, a reference material 22, a static surface 24, optionally, a transparent film 26 and, optionally, printed indicia (not shown) as demonstrated in FIG. 7. Accordingly, these components are given the same reference numerals in FIG. 4 and are not described further here.

Figure 8:
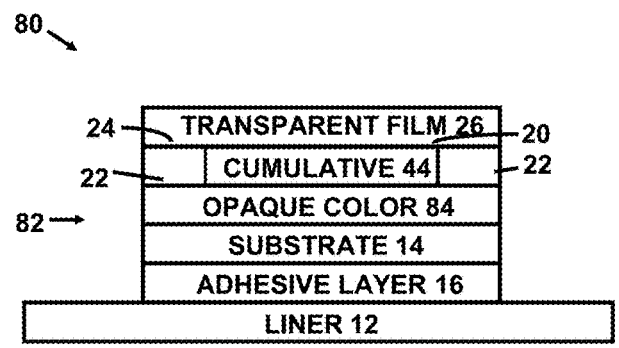
FIG. 8 is a view similar to FIG. 2 of a further example embodiment of the example dual-function heat indicator shown in FIG. 1.
Figure 9:
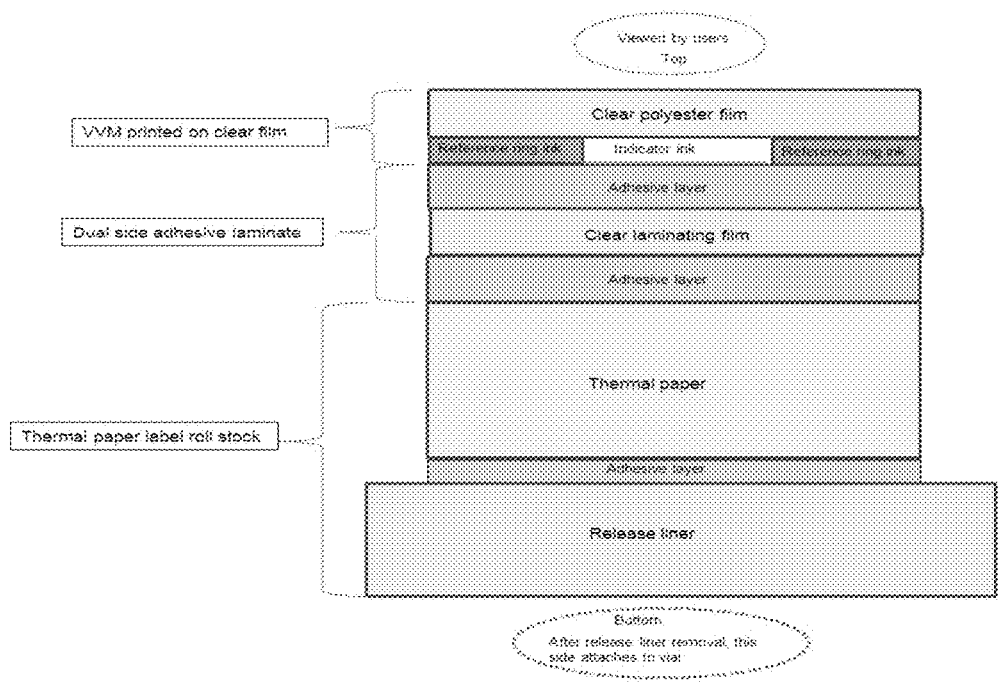
FIG. 9 is a cross sectional view of an example manufactured dual heat indicator prototype discussed in Example 1 herein.

In yet a further example embodiment, dual-function heat indicator 80 for monitoring cumulative ambient heat exposure and peak ambient heat exposure includes a substrate 14, a cumulative exposure indicator supported by the substrate in one viewable layer 44, and a peak exposure indicator 82 which may include meltable particulate colored material 84 supported by substrate 14 in another viewable layer as shown in FIG. 8. Dual-function heat indicator 80 may further include a liner 12, an adhesive layer 16, an active surface 20, a reference material 22, a static surface 24, optionally, a transparent film 26 and, optionally, printed indicia (not shown). The cumulative exposure indicator 44 may be color-changeable in response to cumulative ambient heat exposure, and the peak exposure indicator 82 may include a meltable particulate colored material 84. In this example embodiment, the meltable particulate colored material 84 may have an average particle size imbuing the meltable particulate colored material 84 with a light color, the light color being attributable to scattering of visible light by the meltable particulate colored material 84. Optionally, the meltable particulate colored material 84 may include a meltable solid and a dye dissolved in the meltable solid.

Melting of the meltable particulate colored material 84 may cause the meltable particulate colored material 84 to darken in color and the darkening may be irreversible so that the peak exposure indicator 82 provides an irreversible signal. The darkening may be induced by an ambient heat exposure peak reaching a temperature exceeding the melting point of the meltable particulate colored material 84. Thus, dual-function heat indicator 80 may indicate cumulative ambient heat exposure or peak ambient heat exposure by changing color.

Prior to activation, the meltable particulate colored material 84 may give peak exposure indicator 82 a light color due to light scattering. When the meltable particulate colored material 84 softens or melts in response to ambient heat exposure peak, the small colored particles may coalesce, merge and/or fuse, to provide one or more larger coalesced masses or agglomerations that may exhibit the inherent color of the colored material. The inherent color may be a dark, or strongly colored appearance that the colored material exhibits in bulk, for example, in a continuous film. The inherent color may also be opaque. The meltable particulate colored material 84 may obscure any background behind the meltable particulate colored material 84 so that the background may not be viewed accurately through the meltable particulate colored material 84. Employing a dye or other colorant, or by using a meltable solid having an inherent color, dark or strong colors, such as an intense red, or black, may be displayed so that the peak exposure indicator 82 exhibits good contrast between its appearances before and after activation, such as is described elsewhere herein.

The meltable particulate colored material 84 may provide a color change without significant migration of the meltable particulate colored material 84 or a meltable component thereof. For example, the meltable particulate colored material 84 may remain immobile within one layer of dual-function heat indicator 80. However, some small-scale migration of the meltable particulate colored material 84 may occur as the particles melt and coalesce, or merge, with adjacent particles, possibly forming a film, or coherent area or areas of colored material, or simply to form larger particles that are visible. Further, the meltable particulate colored material 84 may provide a color change non-chemically, without reacting with a color developer or otherwise entering into a chemical reaction.

Various meltable solids may be employed as a component of the meltable particulate colored material 84, as will be known or apparent to a person of ordinary skill in the art, in light of this disclosure, or will become known or apparent in the future. Some examples of suitable meltable solids include alkanes, alkyl esters, undecane, dodecane, tridecane, tetradecane, pentadecane, hexadecane, heptadecane, octadecane, nonadecane, eicosane, heneicosane, hexanoic acid, hexadecane and ethyl lactate, waxes, wax materials such as a paraffin wax, a microcrystalline wax, carnauba wax, beeswax, Chinese wax, shellac wax, spermaceti, tallow, palm wax, soy wax, lanolin, wool grease, a waxy polymer, a waxy copolymer, a polyolefin, polyethylene, polypropylene, an ethylene-vinyl acetate copolymer, an ethylene-acrylic acid copolymer and mixtures of any two or more of the foregoing wax materials. Some other materials useful as meltable solids in this aspect of the example embodiment of the invention include the thermal sensitizers described herein. A meltable solid having a melting point corresponding with a desired threshold temperature for the peak exposure indicator may be selected. The meltable particulate colored material 84 may be formulated without employing a solid side-chain crystallizable polymer, if desired. Some meltable solids may be selected according to how their glass transition temperatures relate to the desired threshold temperature, if appropriate. Thus, the threshold temperature of the peak exposure indicator may be varied by suitable selection of the meltable solid, with due allowance for the effect of the dye upon the melting point of the meltable solid, if any.

Further example embodiments of the invention may include protection from ultraviolet radiation, if desired. Ultraviolet radiation may interfere with the response of a dual-function heat indicator, in some cases, and may degrade a variety of materials. Ultraviolet protection may be provided in any one or more of various ways. For example, one or more ultraviolet filter materials may be included in transparent film 26. In another example embodiment, a visibly transparent ultraviolet-filtering layer, such as a printed ultraviolet-absorbent ink may be disposed directly over active surface 20. Such a construction is described in U.S. Pat. No. 7,682,830 to Prusik et al. A further way to provide protection against ultraviolet radiation is for the adhesive used to attach an outer protective transparent film, such as transparent film 26, if a transparent film and adhesive are employed, to include one or more ultraviolet filters. Such a construction is described in U.S. Provisional Patent Application No. 61/611,319 to Smith et al. The ultraviolet protection measures described in U.S. Pat. No. 7,682,830 and Application No. 61/611,319 may be employed in an example embodiment of the dual-function heat indicator, as will be apparent to a person of ordinary skill in the art Various dyes or other colorants or optically distinctive materials may be dissolved in, or otherwise incorporated in a meltable solid employed in the practice of the example embodiment of the invention to give the meltable solid a distinctive inherent appearance, as will be known or apparent to a person of ordinary skill in the art, in light of this disclosure, or will become known or apparent in the future. Examples of suitable dyes include Oil Black BS (C. I. Solvent Black 7 mixed with stearic acid, Orient Corporation of America, Kenilworth, N.J.) and Oil Red O dye (Sigma-Aldrich, St. Louis, Mo.). Optionally the dye or other colorant or optically distinctive material and/or the meltable solid may be opaque so that the peak exposure indicator has an opaque appearance after activation. Some other optically distinctive materials that may be employed include pigments, fluorescent materials, pearlescent materials, iridescent materials and mixtures of two or more of the foregoing optically distinctive materials.

An example embodiment of a method of preparing a peak exposure indicator employing a meltable particulate colored material 84 configured into light-scattering particles for inclusion in an example embodiment of a dual-function heat indicator will now be described. The method includes dissolving a relatively small amount of dye in a meltable solid formed of an organic material such as a wax, for example from about 0.001 percent to about 1 percent by weight of the dye based upon the weight of the resultant meltable colored material. The meltable solid may be light in color, for example white or pale yellow, and optionally, may be transparent or translucent. Sufficient dye may be employed to color the meltable solid while avoiding an excess, for example, 0.02 percent by weight of Oil Black BS (C. I. Solvent Black 7 mixed with stearic acid), which is an intense black powder, may be dissolved in heneicosane. Heneicosane is a linear $C_{21}$ light-colored, or whitish, alkane having a melting point of about 40° C. that is available from Sigma-Aldrich (St. Louis, Mo.).

This method may also include preparing fine particles of the meltable colored material having an average particle size providing a light-colored appearance of the dyed wax may be prepared by any suitable size-reduction procedure. Some examples of suitable size-reduction procedures include emulsifying the meltable colored material at a temperature above its melting point, when the material is molten, then cooling the resultant emulsion, or precipitating the molten colored material into cold water, or another non-solvent, with vigorous mixing. Other suitable size-reduction procedures will be known or apparent to a person of ordinary skill in the art, in light of this disclosure, or will become known or apparent in the future. The sizing procedure may be conducted to yield an average particle size in the range of from about 50 nm to about 5 µm, in the range of from about 100 nm to about 2 µm, in the range of from about 200 nm to about 700 nm, or in the range of from about 200 nm to about 350 nm. The parameters of the sizing procedure may be varied to provide a desired degree of light scattering, which optionally may be determined by the desired lightness of the meltable particulate colored material so prepared. The resultant particles may have an average particle size of at least about 50 nm, 10 nm, or 200 nm, and of not more than about 350 nm, 700 nm, 2 µm or 5 µm.

The method may further include formulating a coating composition incorporating the meltable particulate colored material and applying the coating composition to the substrate. Other ingredients such as thermal sensitizers, binders, pigments, lubricants, dispersants, antifoam agents, and the like, including the materials described herein, optionally, may also be employed in the coating composition. If employed, such other ingredients should have optical properties compatible with the intended optical performance of the peak exposure indicator.

The coating composition may be prepared by a method such as is described herein for preparing a peak indicator composition except that the first reactant and the second reactant are omitted. Thus, the color-forming function of the first reactant and the second reactant may be replaced by the meltable particulate colored material. Using the previously described example of a black-dyed heneicosane wax, the dyed wax particles may have a light color, for example, whitish, due to light scattering, prior to activation of the peak exposure indicator. However, upon melting of the heneicosane wax, in response to exposure to an ambient temperature at, or above, about 40° C., the melting point of the heneicosane wax, the inherent black color of the dyed wax particles quickly becomes apparent. Promptly after melting the small dyed wax particles coalesce and cease scattering light revealing their inherent color.

In a further aspect, the example embodiment of the invention provides a heat event indicator for monitoring ambient heat exposure to a temperature traversing a threshold temperature. The heat event indicator may include a substrate and a coalesceable particulate colored material supported by the substrate. The coalesceable particulate colored material may have an average particle size imbuing the coalesceable particulate indicator material with a light color, the light color being attributable to scattering of visible light by the coalesceable colored material particles. Coalescence of the coalesceable particulate colored material may cause the material to darken in color, and the darkening may be induced by an ambient heat exposure event that reaches a temperature traversing the threshold temperature. Thus, the heat event indicator may indicate the occurrence of the ambient heat exposure event by changing color.

In such a heat event indicator, the threshold temperature may be a peak temperature and the coalesceable particulate colored material may be meltable and may melt in response to the ambient heat exposure event. Such embodiments of heat event indicator may be similar to a dual-function heat indicator as described herein wherein the peak exposure indicator component of the dual-function heat indicator employs a light-scattering meltable particulate colored material and no cumulative exposure indicator is present. The coalesceable particulate colored material may be similar to a meltable particulate colored material and may have an average particle size as described for the meltable particulate colored material. Further, the coalesceable particulate colored material may provide a color change, in response to a suitable heat event, without reacting with a color developer or other chemical reactant and without significant migration after melting. Such a heat event indicator may function as a peak exposure indicator.

Alternatively to a peak temperature, the threshold temperature may be a freezing temperature, the heat event indicator may include a dispersion of the coalesceable particulate colored material in an aqueous liquid medium, wherein the dispersion collapses and the coalesceable particulate colored material coalesces in response to the ambient heat exposure event. Such a heat event indicator may include a transparent layer, a substrate, an adhesive layer, and a liner, all as described herein as one or more optional components.

Initially the inherent color of the coalesceable particulate colored material may be masked by light scattering attributable to the average particle size of the coalesceable particulate colored material providing the dispersed material a lighter appearance, for example, white, whitish or, in the case of an inherently black coalesceable particulate colored material, pale grey, possibly. Also, the light scattering-induced appearance may be opaque. Freezing and/or thawing of the aqueous liquid medium may induce coalescence causing the particles of colored material to reveal their inherent color, which may be darker or more intense than the initial color. After freezing, the colored material may also obscure any background behind the colored material so that the background may not be viewed accurately through the colored material. As described for the meltable particulate colored material, the coalesceable particulate colored material may change color without employing a color developer or a side-chain crystallizable polymer or engaging in a chemical reaction. Such a heat event indicator may function as a freeze indicator.

The dispersed coalesceable particulate colored material may have various components, as will be known or apparent to a person of ordinary skill in the art, in light of this disclosure, or will become known or apparent in the future. In one example embodiment, the colored material may include, or consist of, a dye, such as described herein, dissolved in a suitable hydrophobic liquid, such as an oil, and the oil may be dispersed in the aqueous liquid medium as appropriately sized droplets, providing an emulsion. Suitable oils and other useful characteristics that such a freeze indicating embodiment of the heat event indicator described herein are described in U.S. Pat. No. 8,430,053B2 by Taylor et al.

In another example embodiment, the colored material may include a finely divided pigment dispersed in the oil droplets, in place of, or together with the dissolved dye. In a further example, pigment particles of an appropriate size to cause light scattering may provide the colored material and no oil or dye need be employed.

MATERIALS

Various materials that may be employed in the practice of the example embodiments of the invention detailed above will now be described. It will be known or apparent to a person of ordinary skill in the art, in light of this disclosure, other materials that may also be suitable.

Liner.

Suitable liner materials for dual-function heat indicator embodiments of the example embodiment of the invention include various papers and synthetic polymer materials, any of which may be coated to facilitate removal of a dual-function heat indicator having an adhesive-coated substrate from a liner. Other suitable liner materials will be known or apparent to a person of ordinary skill in the art. Some suitable papers include kraft paper, calandered kraft paper, machine glazed paper, and clay-coated paper. Some suitable synthetic polymeric materials include polyethylene terephthalate, biaxially oriented polypropylene and polyolefins. Some suitable coating materials include polyvinyl alcohol, silicones, and other materials having low surface energy.

Substrate.

A substrate employed in an example embodiment of the dual-function heat indicator may be fabricated from a variety of materials including imprintable or coatable materials, for example, a synthetic plastic sheet or film. Other suitable substrate materials will be known or apparent to a person of ordinary skill in the art. Suitable substrates may be flexible or rigid, transparent or opaque, optionally may be colored, and may be lamina in form, or sheet-like. White substrates may help provide contrast with an end point appearance if the cumulative heat indicator and peak exposure indicator are initially transparent. Also, where the indicators are initially transparent, distinctive indicia, or a graphic, for example a check mark, or other suitable human-readable or machine-readable indicia may be included on the substrate, and may be obscured after the dual-function heat indicator transitions to an end point appearance. For mass production, substrates for individual indicators may be cut from sheets, strips, or continuous webs. Some examples of useful substrate materials include, without limitation, polyethylene, polypropylene, polycarbonate, polyester, polyamide, polyurethane, polyvinyl chloride, polyvinylidene chloride, cellulose-derived materials, aluminum foil, paper, coated paper, and a laminated structure including a layer or layers of any one or more of the foregoing materials.

A further example of a suitable substrate material is a corona-treated, dimensionally stable, flexible, white, opaque polyolefin film such as is supplied under the trademarks FASSON® PRIMAX®, product code 250, by Avery Dennison Corporation, Pasadena, Calif.

Optionally, in example embodiments of the invention where a substrate contacts an adhesive material, the substrate surface may be sealed or otherwise treated to inhibit migration of the adhesive or components of the adhesive through the substrate material. Alternatively, or in addition a substrate material, or an additional material layer, that resists such migration may be employed.

Cumulative Exposure Indicator.

The cumulative exposure indicator employed in an example embodiment of the dual-function heat indicator may be or may include a heat-sensing agent that may change appearance in response to heat. The heat-sensing agent may darken in color with continued heat exposure, and the degree of darkening may provide a measure of the cumulative heat exposure. Alternatively, the heat-sensing agent may exhibit another appearance change, for example, lightening, a change in hue, or another optically readable indication. The heat-sensing agent may include one or more heat-sensitive compounds, some of which are described elsewhere herein.

The cumulative exposure indicator may be manufactured by applying a suitable indicator ink including the heat-sensing agent to a substrate, then drying the indicator ink on the substrate, as described elsewhere herein. The cumulative exposure indicator may include the dried residue of the ink and the substrate supporting the ink residue. The indicator ink may include a liquid vehicle; a film-forming agent dissolved in the liquid vehicle, an insoluble heat-sensing agent dispersed in the liquid vehicle and various optional ingredients for example one or more dispersants, antiactinic agents, colorants, preservatives, fragrances or other additives. An example of a suitable liquid vehicle is an organic solvent such as isopropanol, or ethyl 3-ethoxypropionate. An example of a suitable film-forming agent is nitrocellulose. Some examples of suitable indicator inks that may be employed in dual-function heat indicator embodiments of the example embodiment of the invention and their manufacture are described in U.S. Pat. No. 8,067,483 and the patent documents referenced therein.

Some useful heat-sensing agents may provide an irreversible indication of cumulative temperature exposure over time, and may provide a long-lasting record of the heat exposure. The cumulative heat response of the heat-sensing agent may be such that the heat-sensing agent may monitor heat exposure as an integral of temperature over time. Further, the heat-sensing agent may be heat-sensitive and may have useful indicator reactivity at ambient temperatures likely to be encountered by a monitored host product, for example, temperatures in the range of from about 0° C. to about 60° C.

The heat-sensing agent may include, or consist of, any of a variety of chemical components. One useful example embodiment of heat-sensing agents includes one or more thermally sensitive diacetylenic compounds, for example, an individual diacetylenic compound or a co-crystallized mixture of two diacetylenic compounds.

The diacetylenic compound, or compounds, may polymerize to provide a color change or another optically readable indication. Diacetylenic compounds useful in the practice of the example embodiment of the invention include polymerizable diacetylenic compounds including at least two conjugated acetylenic groups, i.e. groups having the formula —C≡C—. Some exemplary polymerizable diacetylenic compounds that may be employed include substituted 2,4-hexadiyn-1,6-bis(alkylurea) compounds wherein the alkyl group has from 1 to 20 carbon atoms, the foregoing diacetylenic bis(alkylurea) compounds wherein the alkyl substituents are linear, and co-crystallized mixtures of any two or more of the foregoing bis(alkylurea) compounds. The two alkyl groups in any of the foregoing diacetylenic bis(alkylurea) compounds may be the same and the bis(alkylurea) compounds may be symmetrically substituted. Some particular examples of the foregoing diacetylenic bis(alkylurea) compounds include ethyl, propyl, butyl, octyl, dodecyl and octyldecyl-substituted 2,4-hexadiyn-1,6-bis(alkylurea) compounds, linear isomers of these compounds and co-crystallized mixtures of two or more of the linear isomers.

Some further example embodiments of useful diacetylenic compounds that may be employed in example embodiments of the dual-function heat indicator are disclosed in U.S. Pat. Nos. 3,999,946; 4,189,399 and 4,384,980 to Patel; U.S. Pat. Nos. 4,789,637 and 4,788,151 to Preziosi et al.; U.S. Pat. Nos. 6,924,148; 7,019,171; 7,161,023; and 8,067,483 to Prusik, or Prusik et al.; U.S. Patent Application Publication No. 2009/0131718 by Baughman et al.; and U.S. Patent Application Publication No. 2011/0086995 by Castillo Martinez et al., among which documents the latter three were cited previously herein. Some useful heat-sensing agents may include one or more diacetylenic compounds and a reactivity-enhancing adjuvant, for example, as described in U.S. Pat. No. 8,067,483. Useful diacetylenic compounds are also described at page 36, line 10 to page 39, line 4 of Provisional Patent Application No. 61/611,319 filed Mar. 15, 2012.

Other chemistries and technologies that may be used as, or in, a heat-sensing agent for a cumulative exposure indicator component of an example embodiment of a dual-function heat indicator include:

heat-sensitive dyes that may be activated or de-activated by exposure to ultraviolet radiation to provide or remove color;

dyes that are triggered to exhibit color, or change color, by pH changes, for example, as disclosed in U.S. Pat. No. 4,917,503 to Bhattacharjee;

a reversibly photochromic compound, such as a compound that may undergo photo-induced coloration by irradiation with light or ultraviolet radiation, followed by a time- and temperature-dependent decoloration, for example, a spiroaromatic compound, some examples of which are described in U.S. Patent Application Publication No. 2010/0034961 by Tenetov et al. ("US 2010/0034961"); and enzyme-based sensors such as are described in U.S. Pat. No. 6,642,016 to Sjoholm, et al. or U.S. Pat. No. 4,284,719 to Agerhem, et al.

Some further example embodiments of useful cumulative exposure indicators that may be employed in practicing the example embodiment of the invention are described in U.S. Pat. No. 5,622,137 to Lupton et al., U.S. Pat. No. 5,756,356 to Yanagi, et al., U.S. Pat. No. 6,043,021 to Manico et al., and International Publication No. WO 99/39197 by Haarer et al. Still further suitable cumulative exposure indicators that may be employed in practicing the example embodiment of the invention will be known or apparent to a person of ordinary skill in the art, in light of this disclosure, or will become known or apparent in the future.

Peak Exposure Indicator.

The peak exposure indicator may be a meltable solid and may include a first reactant and a second reactant that are chemically co-reactable to provide a color change. Further the peak exposure indicator may be a reactant, it may include one or more reactants, it may separate the reactants, or it may be the agent which on melting enables the reactants to react. Optionally, a thermal sensitizer may also be included. The first reactant and the second reactant may be present in the same layer of an example embodiment of the dual-function heat indicator. Alternatively, the first reactant and the second reactant may be present in different layers of an example embodiment of the dual-function heat indicator. The color-changing chemical reaction may be induced in response to an ambient heat exposure peak and may be irreversible. Optionally, a single reactant may provide suitable peak exposure indicating functionality.

The peak exposure indicator may include additional ingredients that contribute to the useful functioning of an example embodiment of the dual-function heat indicator.

Some examples of possible additional ingredients, which may be employed individually or in combination, include pigments, binders, lubricants, dispersants, antifoam agents, and other additives that may modify one or more characteristics of the peak exposure indicator, without detracting from its performance, as will be known or apparent to a person of ordinary skill in the art, in light of this disclosure, or will become known or apparent in the future. Such additional ingredients, if present, also may be included in a single layer with the first reactant and the second reactant.

By way of example, the first reactant may be a color precursor, or color former, and the second reactant may be a color developer. Many suitable color precursors and color developers are known and may be employed alone or in combinations of two or more compatible compounds. Some suitable color-forming reactants, including some color precursors and color developers, are described in U.S. Pat. No. 8,430,053 to Taylor et al., for example, at paragraphs [0199] to [0248]. Suitable color-forming reactants are also described in U.S. Pat. No. 5,741,592 to Lewis et al. and U.S. Patent Application Publication No. 2008/0233290 to Ward-Askey et al.

Some specific examples of useful color precursors include: specialty magenta 20, ODB-1 and ODB-2 (available from Emerald Hilton Davis, Cincinnati, Ohio); and PERGASCRIPT® Red 16B (available from BASF, Charlotte, N.C.). Upon development, specialty magenta 20 and PERGASCRIPT® Red 16B produce an intense magenta color, and color precursors ODB-1 and ODB-2, become black.

Some further examples of useful color precursors include: benzoyl leuco methylene blue; malachite green lactone; N-2,4,5-trichlorophenylleuco auramine; additional compounds that are red when developed including 3-diethylamino-6-methyl-7-chlorofluoran, and 3,6-bis(diethylamino) fluoran-γ-(4'-nitro)-anilinolactam; additional compounds that are black when developed including 3-diethylamino-6-methyl-7-anilinofluoran and 3-(N-ethyl-N-isoamylamino)-6-methyl-7-anilinofluoran; and compounds that are orange when developed including 3-cyclohexylamino-6-chlorofluoran and 3-diethylamino-6,8-dimethylfluoran.

Still further examples of useful color precursors include: 3,3-bis(p-dimethylaminophenyl)-phthalide; 3,3-bis(p-dimethylaminophenyl)-6-dimethylaminophthalide (crystal violet lactone); 3,3-bis(p-dimethylaminophenyl)-6-diethylaminophthalide; 3,3-bis(p-dimethylaminophenyl)-6-chlorophthalide; 3,3-bis(p-dibutylaminophenyl)-phthalide; 3-(N—N-diethylamino)-5-methyl-7-(N,N-dibenzylamino) fluoran; 3-dimethylamino-5,7-dimethylfluoran; 3-diethylamino-7-methylfluoran; 3-(2'-hydroxy-4'-dimethylaminophenyl)-3-(2'[-methoxy-5'-chlorophenyl)phthalide; 3-(2'-hydroxy-4'-dimethylaminophenyl)-3-(2'-methoxy-5'-nitrophenyl-phthalide; 3-(2'-hydroxy-4'-diethylaminophenyl)-3-(2'-methoxy-5'-methylphenyl) phthalide; and 3-(2'-methoxy-4'-dimethylaminophenyl)-3-(2'-hydroxy-4'-chloro-5'-methylphenyl)-phthalide.

Some specific examples of useful color developers include oil-soluble reducing agents; oxalic acid; phosphite esters; hydroxybenzoic acid esters; hydrohydroquinone, hydroquinone derivatives such as dimethyhydroquinone, di-tert-butyl hydro quinone, other dialkylhydroquinones, and the like, 3-ethoxyphenol; 1,2-diethyl-3-hydroxybenzene; 1,3-diethyl-2-hydroxybenzene; 2,2'-methylenebis(3,4,6-trichlorophenol); meltable, or sensitizer-soluble, primary and secondary amines having low water solubility, for example, 4-butyl-aniline; phenol derivatives; organic acids; acid clays; FULACOLOR™ XW reactive acid hectorite clay (available from Rockwood Additives, Widnes, UK); phenolic resins; phenol-acetylene resins; polyvalent metallic salts of phenolic resins; HRJ 2053 zinc-including modified alkyl phenolic resin (available from SI Group, Schenectady, N.Y.); zinc salicylate, zinc salicylate resin; 4,4'-isopropylidenebisphenol (also known as bisphenol A); 1,7-di(hydroxyphenylthio)-3,5-dioxaheptane, 4-hydroxyethyl benzoate, 4-hydroxydimethyl phthalate; monobenzyl phthalate; bis-(4-hydroxy-2-methyl-5-ethylphenyl)sulfide, 4-hydroxy-4'-isopropoxydiphenylsulfone; 4-hydroxyphenylbenzenesulfonate; 4-hydroxybenzoyloxybenzylbenzoate; bis-(3-1-butyl-4-hydroxy-6-methylphenyl)sulfone; p-tert-butylphenol; and polymers based on bisphenol A.

Thermal Sensitizers.

A thermal sensitizer optionally may be employed in an example embodiment of the peak exposure indicator. A thermal sensitizer may be selected to have a melting-point that causes the peak exposure indicator to at least begin to melt at a desired response temperature, initiating the color-changing reaction.

The thermal sensitizer may be mixed with the first reactant and the second reactant and the resultant mixture may have a melting-point that is the same as the desired response temperature or within about 2° C., or about 5° C. of the desired response temperature of the peak exposure indicator. The mixture may be an intimate admixture of the ingredients in particulate form. Alternatively, the melting-point of the thermal sensitizer may be the same as the desired response temperature or may be within about 2° C., or about 5° C. of the desired response temperature. Where no thermal sensitizer is employed, at least one of the first reactant and the second reactant may have a melting point that is the same as the desired response temperature or is within about 2° C., or about 5° C. of the desired response temperature.

The thermal sensitizer, if employed, may help control the melting-point of the peak exposure indicator, for example by lowering the melting-point and may initiate or accelerate the color-forming reaction.

Some materials useful as thermal sensitizers in the practice of the example embodiment of the invention may include fatty acid amide compounds, acetamide, stearic acid amide, linolenic acid amide, lauric acid amide, myristic acid amide, methylol compounds, methylene-bis(stearamide), ethylene-bis(stearamide), p-hydrozybenzoic acid esters, methyl p-hydroxybenzoate, n-propyl p-hydroxybenzoate, isopropyl p-hydroxybenzoate, benzyl p-hydroxybenzoate, diphenoxyethane, aryl-substituted biphenyls, alkyl-substituted biphenyls, p-benzyl biphenyl, toluidide phenyl, heptadecanol, 4-methoxyphenol, pentadecanol, 2,4-di-tert-butyl phenol, benzophenone, diethyl terephthalate hydroxynaphthoates, alkyl alcohols, and dibenzyl oxalate any of which materials may be used alone or in combination. Useful thermal sensitizers optionally may include a wax and/or a fatty acid.

Some materials useful as binders in the practice of the example embodiment of the invention include starches, celluloses, natural and synthetic gelatins, methoxycellulose, hydroxyethylcellulose, carboxymethylcellulose, polyvinyl alcohol, polyvinylpyrrolidone, polyacrylamide, polyacrylic acid, copolymers of vinyl chloride and vinyl acetate, polybutylmethacrylate, and water emulsions of polystyrene. Two or more binder materials may be employed. The binder, if employed, may be water insoluble, water soluble or a mixture of one or more water-insoluble binder materials, and one or more water-soluble binder materials.

Some materials useful as pigments in the practice of the example embodiment of the invention include calcium carbonate, silica, titanium dioxide, alumina, magnesia, talc, barium sulfate and aluminum stearate.

Some materials useful as lubricants in the practice of the example embodiment of the invention include linseed oil, tung oil, wax, paraffin, and polyethylene wax.

Other suitable materials will be known or apparent to a person of ordinary skill in the art, in light of this disclosure, or will become known or apparent in the future.

Dual-function exposure indicators according to the example embodiment of the invention may usefully be employed to monitor the condition of any of a wide range of heat-sensitive host products. Host products that may be monitored include, in addition to vaccines: temperature-sensitive health care products, for example, drugs, medicaments, pharmaceuticals, pharmaceuticals incorporating a polypeptide, a nucleic acid or cellular material, temperature-sensitive medical devices, temperature-sensitive prophylactics and the like; biological materials for industrial or therapeutic uses, for example cultures, organs, and other human or animal body parts, blood, and perishable blood products; diagnostic devices, diagnostic kits containing perishable products, and perishable diagnostic ingredients; batteries, battery-containing devices, battery-containing appliances; fresh or prepared foodstuffs, including fish, meats, dairy products, fruits, vegetables, baked goods, desserts, and the like; food service products, including restaurant service foods; gourmet food products; perishable animal foods; cut and uncut flowers; plants; cosmetics, for example cosmetics containing biologicals or other labile or perishable ingredients; beauty aids; perishable industrial products; paint; solder; perishable munitions and ordnance; and perishable decontamination packs and products.

A dual-function exposure indicator according to the example embodiment of the invention may be associated with a host product in a variety of ways, for example by adhering, tying, looping, stapling or otherwise affixing the dual-function exposure indicator, or a label or tag embodying the dual-function exposure indicator, to a desired host product, either directly to a host product, or to a package containing the host product, or to a package, carton, box or other container containing a number of host product items. Also, the dual-function exposure indicator, label, or tag, may be inserted in a host product package, carton, or other container for one or more host product items.

EXAMPLES

Example 1: Manufacture of Dual Heat Indicator Prototypes

Prototype indicators were manufactured by laminating VVM14-like cumulative heat indicators, printed on clear film, to a commercially available thermal paper or pre-manufactured thermal paper. VVM14-like cumulative heat indicators are prototype cumulative heat indicators formulated to respond to approximately 14 days at 37° C., and intended to be similar to the commercially available HEATmarker VVM14, available from Temptime Corporation. VVM14 has a well-characterized temperature response profile and is manufactured to meet World Health Organization requirements provided in PQS Performance Specification, Vaccine Vial Monitor WHO/PQS/E06/IN05.2, 26 Jul. 2011. It responds in 14 days at 37° C., in 90 days at 25° C., and >3 years at 5° C. The prototype indicators were manufactured on a Gallus 250 I printing press. Two trials were performed, the latter was to evaluate a thinner version of the clear polyester film as an improvement. Neither set of prototypes were die-cut on the Gallus press to avoid the cost of obtaining die tools, however they were manually die-cut to produce samples for demonstration. The trials demonstrated that the process and the prototype construction were feasible. The prototypes were able to detect excessive heat exposure and still monitor the cumulative effects of heat and time below the threshold limit.

The first trial used DuPont Teijin Films™ Melinex® 561, a 0.005 inch thick, clear polyester film. This film is chemically treated on both sides to accept solvent-based inks and provide a clean cut when die-cutting. The second prototype trial utilized Transilwrap Company general purpose Oriented Polyester, a 0.00092 inch thick, clear polyester film treated on one side for solvent-based printing. Gotham Ink's "Gotham baseline lavender", a solvent-based flexographic ink adjusted to obtain an exact color match with the indicator ink by adding suitable quantities of Gotham Series opaque white, Gotham Series magenta, and Gotham Series cyan inks was utilized for the reference ring ink. The indicator "active" ink was manufactured in-house by dispersing "KE" (2,4-hexadiyn-1,6-bis(ethylurea)) powder in a solvent-based nitrocellulose ink, according to the procedures outlined in U.S. Pat. No. 8,067,483. The quantity of KE in the ink and the amount of ink applied to the polyester film were chosen in order to achieve a color match between the temperature-sensitive active ink and the temperature-insensitive reference ink after about 14 days at 37° C.

FLEXcon's FLX055158 FLEXmount DFM-100 Clear V-224 150 Poly H-9 V-224 150 Poly H-9 laminate was utilized. This laminate consists of a clear polyester carrier film, coated both sides with a water-based permanent pressure-sensitive adhesive. It was used for laminating the thermal paper to the printed clear polyester film. The laminate was provided with release liners on both sides, which were removed during prototype manufacture. Earlier screening demonstrated that solvent based adhesives may affect the ability of the thermal paper to darken as such this water-based adhesive was selected because it did not show that effect. However, there may be suitable combinations of solvent-based adhesives with thermal paper that do not show this effect. The polyester carrier film and the two layers of adhesive add 0.003 mm to the laminated structure thickness. Each adhesive layer is 0.001 mm thick on a 0.001 mm PET carrier film. If further reduction in stiffness and thickness are required in the product, this laminating film could be replaced with an unsupported adhesive layer applied as a transfer tape product.

The thermal paper utilized was Mactac DTR 9902 thermal label paper, consisting of high sensitivity topcoated IR scanable direct thermal paper with a high tack permanent acrylic emulsion adhesive, supplied with a semi-bleached calendared kraft liner. The thermal paper thickness is described as typically 0.0034 in and the adhesive adds another 0.0007 in to the thickness. The adhesive is designed for use on medical vials and has an average peel strength of 2.4 lbs/in. The adhesive was designed to adhere to metal, plastic and glass.

The process of manufacturing consisted of a first pass through the Gallus press to form a laminate between the thermal paper and the dual side adhesive coated laminating film. The thermal paper was placed on the unwind roller with the active surface facing up. The corona treater and dryers were off and cold for this step. If either were on, it could have caused the thermal paper to darken. At the laminating station, the Flexmount DFM was mounted so that one liner was removed and the newly revealed adhesive was placed in contact with the thermal paper's active surface. The resulting laminated product was rewound so that it could be used on the laminating station in the second pass.

The second pass at the press consisted of the clear polyester film being placed at the unwind. In the first trial, there was no need to be careful of which side would be printed because both sides were chemically treated for solvent ink acceptance. In the second trial however, the clear polyester film had the chemically treated side only on the outside surface of the roll, so care was taken to mount the roll so that the outside would be printed.

In order to manufacture the cumulative indicator portion of the dual indicator, the reference ring was printed onto the clear polyester first followed by two printed layers of the active ink.

The rolls made in the first pass through the press were mounted at the laminating station so that the release liner from the other adhesive surface of the dual side adhesive coated laminating film was removed. The newly revealed adhesive came into contact with the printed cumulative indicator on the clear polyester film. The entire laminate was flipped so that the clear polyester film was on top. This configuration would then be ready to be die-cut through the clear polyester down through to the release liner of the thermal paper. No die-cutting was performed in these trials.

The results for the samples from the first prototype trial using DuPont Teijin Films™ Melinex® 561 may be seen in FIGS. 10-13. Three types of samples were obtained: the dual indicator construction, just the thermal paper with the laminating film and clear film on top, and just the cumulative indicator portion of the dual indicator (i.e. the active and reference inks printed onto the clear film). Optical density measurements were performed using an X-Rite 504 Spectrodensitometer and the cyan, magenta, yellow and black measurements were recorded. Only cyan optical density measurements are reported and were used for performance analysis comparable to assessments of the active ink portion of the cumulative indicator. The reference ring had a cyan OD value of about 0.50, which was unaffected by temperature exposure. The three sample types were affected by temperature, and in each case the indicator "end point" for any given temperature may be represented by the amount of time for the indicator to reach an OD of about 0.50.

Ten samples of each phase were tested in isothermal water baths capable of controlling the temperature to ±0.1° C. The samples were mounted onto white cardstock then double sealed in aluminum and plastic pouches and held at various temperatures for a series of specified times, periodically removing them from the baths to measure the OD change over time. At higher temperatures, the samples were double bagged in clear plastic so that the response could be observed directly.

At 90° C., the indicator response was dominated by the thermal paper which blackens within 1 second of immersion in the water bath. There was no change in the VVM14-like portion of the indicators in this time frame. Endpoint, defined as when the cyan absolute OD reaches 0.50, was not reached for the cumulative indicators until almost 40 minutes.

At 80° C. the results are similar to those presented for 90° C. except that the thermal paper darkening took a little longer, 10 seconds, and the maximum OD was slightly lower. The cumulative indicators did not reach 0.5 OD until nearly 3 hours. In general, at temperatures of 50° C. and below, the thermal paper showed very little response and therefore the dual heat indicator responded essentially as a cumulative indicator.

Example 2: Dual Heat Indicator Protoypes to Illustrate Example Embodiment Demonstrated in FIG. 7

Hand-made prototype dual heat indicators were made by laminating VVM14-like cumulative heat indicators, printed on clear film, to a commercially or pre-manufactured available threshold indicator. The cumulative indicator component was made by printing a color-changing "active" diacetylene ink and a static, "reference ink" onto DuPont Teijin Films™ Melinex® 561, a 0.005 inch thick, clear polyester film, using a Gallus 250 I printing press. The "active" ink was manufactured in-house by dispersing "KE" (2,4-hexadiyn-1,6-bis(ethylurea)) powder in a solvent-based nitrocellulose ink, according to the procedures outlined in U.S. Pat. No. 8,067,483. The quantity of KE in the ink and the amount of ink applied to the polyester film were chosen in order to achieve a color match between the temperature-sensitive active ink and the temperature-insensitive reference ink after about 14 days at 37° C. The "reference" ink was Gotham Ink's "Gotham baseline lavender", a solvent-based flexographic ink adjusted to obtain an exact color match with the indicator ink by adding suitable quantities of Gotham Series opaque white, magenta, and cyan inks. This cumulative heat indicator was intended to have similar appearance and time/temperature response to Temptime's HEATmarker® VVM14 indicator.

VVM14-like indicators that were printed on clear film were placed over samples of Temptime's DEGmarker® 40 indicators and taped on the edges onto white card stock (176 g/m$^2$, 8.5 by 11 inches Staples White Card Stock acid free code#733350). Because the active ink is nearly transparent when printed on clear film, the gray center dot of the DEGmarker 40 indicators could easily be seen through the active ink square of the VVM14-like indicators. For comparison, the VVM14-like indicators and the DEGmarker indicators were also included on the card.

The test card with the indicators were placed inside an oven (Boekel Scientific CCC1.4d thermal Incubator), at 25° C., 35° C., 45° C. and held for 5 minutes at each temperature. Optical density (OD) was measured for the active part of each indicator after each 5-minute period using an X-rite 504 Spectrodensitometer and reported for cyan. There was no change of the indicators at 25° C. and 35° C. At 45° C., color change of the dual heat indicator and the DEGmarker indicator was rapid and noticeable and occurred within 2 minutes. The measured optical densities may be seen in FIG. 14. FIG. 15 shows the test card with the indicators at no heating and heating at 45° C.

A second set of experiments were performed where dual heat indicator prototypes were made and placed into heat sealed clear plastic bags so that they could be observed at increments of 1° C. changes in a circulating water bath (Thermo Scientific AC150 containing 60/40 water/propylene glycol). Each sample was placed into the bath at the specified temperature for 5 minutes. Observations were made at about 2 minute intervals by looking into the bath at the samples in the clear plastic bags. OD measurements were not taken. One set of samples was made with DEGmarker 40 threshold indicators, and another set was made in the same way with DEGmarker 45 threshold indicators. Dual heat indicator prototypes made with VVM14 and either DEGmarker 40 or DEGmarker 45 gave responses within a degree or two of the 40° C. and 45° C. respectively. Where color changes were seen, they occurred within 2 minutes of exposure. Since the response of the DEGmarker was seen through the active ink "window" of the VVM printed on clear film when made into the dual heat indicator construction, this construction could be a used as a dual heat indicator according to FIG. 7. A comparison of the color appearance of the active region between the dual indicator prototypes made with VVM14 and either DEGmarker 40 or DEGmarker 45 at the varying temperatures may be seen in FIG. 16. The results show how effective the dual heat indicator prototypes are at lower temperatures in comparison to a cumulative indicator only or peak indicator alone.

Example 3: Demonstration of Peak Indicator with Meltable Activator at a Temperature Above the Activator Melting Point as Illustrated in FIG. 5

Ultratherm product number 004188 is a white direct thermal paper label stock from Wausau Paper, Wausau Wis., with an initial static thermal sensitivity of 75° C. The static sensitivity is a measurement of the temperature at which the reaction of the thermal layer sets in. Initial static thermal temperature is the temperature at which the thermal coating develops an optical density of 0.2 OD units. If thermal paper is used to provide the peak indicator component of a dual indicator, then the initial static sensitivity temperature represents the lower end of the peak indicator response temperature range.

To demonstrate a peak indicator for use in a dual function heat indicator construction, a small amount of ground crystalline benzophenone (product B9300 from Sigma-Aldrich, St. Louis Mo.) was spread thinly onto the printable surface of Ultratherm 004188. The melting point of benzophenone reported by the supplier is 48-49° C. This was placed in an oven at about 50° C. The coating developed black color in less than 90 seconds where the crystals had been. The remainder of the paper remained white. The benzophenone appeared to have melted and penetrated the thermal coating in the areas of black color. Development of the paper by the activator occurred at a temperature much lower than the development temperature of the paper itself, and higher than the melting point of the meltable activator.

Example 4: Peak Indicator with Meltable Activator and Substrate at a Temperature Below the Activator Melting Point Four direct thermal substrates were used for the next example of peak indicators for use in dual function heat indicator constructions. The thermal substrates were pairs of similar construction except that one of each pair was supplied with an additional thin transparent protective coating to improve durability and scratch resistance. Samples of activator with substrates were prepared in the same manner as for Example 3. Temperature exposure experiments were conducted by putting test samples in plastic bags, excluding air so each side of the substrate was against the side of the bag, and then immersing this into a thermostatically controlled water bath (Neslab RTE 17 from ThermoElectron Corp.) at 43° C. Temperature was measured with a mercury thermometer with accuracy of <0.1° C. The samples were observed periodically for color development and the test ended after 40 minutes. FIG. 17 lists the samples, their static thermal sensitivities, as stated by the manufacturer, and the response to contact with the activator.

In all cases benzophenone crystals were visible, and there was no evidence of melting. Yet, when benzophenone was in direct contact with the mixture of materials making up the thermal coating there was color development around the point of contact. The coated samples showed little or no development. By inspection with a microscope it was seen that the development spots for the coated samples were often associated with artifacts in the thermal coating, such as protruding fibers, which are well known to be weak points for barrier coatings, and to be covered by very little coating, or none at all. Where it was intact, the coating appeared to act as a barrier between the activator and the thermal coating.

Example 5: Peak Indicator with Meltable Activator and Substrates with Protective Coating at a Temperature Below and Above the Melting Point The two direct thermal substrates with protective coatings used for samples 113 and 115 in Example 4 were used in this example.

Samples of activator with substrates were prepared in the same manner as for Example 3, and temperature exposure experiments were conducted in the same manner as for Example 4 except that initial temperature was 35° C. The temperature was increased in small steps over the course of several hours. There was no development in these examples after 10 minutes at 44.0° C. The first sign of development was a single spot seen 44.5° C. for sample 113A after 10 minutes. After 20 minutes at 45.0° C. sample 115A, also showed a single development spot. Development in both samples continued during a 10 minute period at 45.5° C. Extensive development was seen for sample 113A after a 10 minute dwell at 46.0° C. and for sample 115A after a further 10 min at 46.5° C. At this temperature it as observed that the benzophenone crystals had melted and developed each example in the adjacent region. Again, the development occurred at temperatures much lower than the static sensitivity of the thermal substrate.

The melting point of the benzophenone used for the above examples was determined separately in the apparatus but with the crystals between two glass microscope cover slips, again inside a polyethylene bag. The starting temperature was 45.0° C. and temperature steps were 0.1° C. in roughly 3 minute intervals. The benzophenone melted at 46.1° C.

In this example the development of the thermal composition occurred at temperatures much lower than the static sensitivity temperature of the thermal substrates but also similarly close to the melting point of the meltable activator, even though the thermal substrates have different thermal sensitivities. The difference between the temperature where development was prevented by the transparent barrier coating and where it proceeded rapidly was not more than two degrees. This example embodiment of a coated thermal substrate and a meltable activator has demonstrated a specific response temperature, stability at temperatures lower than but close to the response temperature, and rapid high visual response from a small temperature transition through the response temperature.

Disclosures Incorporated.

The entire disclosure of each United States patent, each United States patent application, each international patent publication, each foreign patent publication, any other publication, and of each unpublished patent application identified in this specification is incorporated by reference herein, in its entirety, for all purposes. Should a conflict appear to be present between the meaning of a term employed in the description of the example embodiment of the invention in this specification and the usage of the term in material incorporated by reference from another document, the meaning of the term as used herein is intended to prevail. Any reference to an "example embodiment of the invention"

in any incorporated disclosure is to be understood to refer to the example embodiment of the invention described, or claimed, in the incorporated disclosure.

About the Description.

The detailed description herein is to be read in light of and in combination with the descriptions of the background to the example embodiment of the invention and of the brief summary of the example embodiment of the invention where information regarding the written description of the example embodiment of the invention, the best mode of practicing the example embodiment of the invention, or description of modifications, alternatives or other useful embodiments of the example embodiment of the invention may also be set forth explicitly, or implied, as will be apparent to one skilled in the art.

The terms "include," "have," "has," and "contain," and their various grammatical forms, are to be understood as being open-ended and not to exclude additional, unrecited elements or method steps.

Throughout the description, where compositions instruments, devices apparatus, systems, or processes are described as having, including, or comprising specific components or elements, or in the case of processes, specific steps, it is contemplated that compositions instruments, devices apparatus, systems, or processes according to the present example embodiment of the invention may also consist essentially of, or consist of, the recited components, elements or steps.

In this application, where an element or component is said to be included in and/or selected from a list or group of recited elements or components, it should be understood that the element or component may be any one of the recited elements or components, or may be selected from a group consisting of two or more of the recited elements or components.

The use of the singular herein is intended to include the plural (and vice versa) unless the context indicates otherwise.

Also, where the term "about", "approximate", "approximately", or a similar term, is used before a quantitative value, the specific quantitative value itself is to be understood to be included, and to be explicitly recited, unless the description specifically states otherwise.

With regard to processes, it is to be understood that the order of steps or order for performing certain actions is immaterial so long as the described process remains operable. Moreover, two or more steps or actions may be conducted simultaneously, unless the context indicates otherwise. In addition, any proportions recited herein are to be understood to be proportions by weight, based upon the weight of the relevant composition, unless the context indicates otherwise. Also, unless the context indicates otherwise, or suggests otherwise, any methods according to the example embodiment of the invention that are described herein, or one or more steps of the methods, may be practiced at a room temperature in the range of about 20° C. to about 25° C.

The description of the background of the example embodiment of the invention herein may include insights, discoveries, understandings or disclosures, or associations together of disclosures, that were not known in the relevant art prior to the present example embodiment of the invention but which are provided by the example embodiment of the invention, and are to be considered elements of the example embodiment of the invention. Some such contributions of the example embodiment of the invention may have been specifically pointed out as being attributable to the example embodiment of the invention, and other such contributions of the example embodiment of the invention will be apparent from their context. Merely because a document may have been cited in this application, no admission is made that the field of the document, which may be quite different from that of the example embodiment of the invention, is analogous to the field or fields of the present example embodiment of the invention.

The description of the example embodiment of the invention herein is to be understood as including combinations of the various elements of the example embodiment of the invention, and of their disclosed or suggested alternatives, including alternatives disclosed, implied or suggested in any one or more of the various methods, products, compositions, systems, apparatus, instruments, aspects, embodiments, examples described in the specification or drawings, if any, and to include any other written or illustrated combination or grouping of elements of the example embodiment of the invention or of the possible practice of the example embodiment of the invention, except for groups or combinations of elements that are incompatible with, or contrary to the purposes of the example embodiment of the invention, as will be, or become, apparent to a person of ordinary skill. Further, embodiments of the example embodiment of the invention may have any configuration according to the example embodiment of the invention that is described herein, or is shown in any accompanying drawings, and may employ any compatible ones of the useful materials or structures described herein.

SCOPE OF THE EXAMPLE EMBODIMENT OF THE INVENTION

The present example embodiment of the invention includes the examples and embodiments described herein and other specific forms of the example embodiment of the invention that embody the spirit or essential characteristics of the example embodiment of the invention or of the respective described examples or embodiments.

The foregoing examples and embodiments are in all respects intended to be illustrative of the example embodiment of the invention described herein. It is to be understood that many and various modifications of the example embodiment of the invention, or of an example or embodiment of the example embodiment of the invention described herein will be apparent to those of ordinary skill in the relevant art, or may become apparent as the art develops, in the light of the foregoing description. Such modifications are contemplated as being within the spirit and scope of the example embodiment of the invention or example embodiment of the inventions disclosed herein.

We claim:
1. A dual-function heat indicator comprising:
a substrate;
a cumulative exposure layer supported by the substrate in a viewable, layered configuration, wherein the cumulative exposure layer is configured to undergo an optical change in appearance in response to a cumulative heat exposure; and
a peak exposure layer supported by the substrate in a viewable, layered configuration, the peak exposure layer comprising a meltable solid configured to melt upon exposure to a predetermined peak heat exposure, the peak exposure layer configured to have a light colored appearance due to light scattering, and in response to the melting of the meltable solid the light scattering ceases causing a darkening of the peak exposure layer, the darkening persisting after the meltable solid re-solidifies;

wherein the cumulative exposure layer and the peak exposure layer are functionally separate with visual outputs of the cumulative exposure layer and the peak exposure layer integrated in a single overlapping display.

2. The dual-function heat indicator of claim 1, wherein the response of the peak exposure layer is not immediate upon exposure to a peak temperature.

3. The dual-function heat indicator of claim 2, wherein the peak exposure layer is configured to darken in response to exposure to the peak temperature after an exposure of at least two minutes.

4. The dual-function heat indicator of claim 1, wherein the peak exposure layer darkens in response to a peak temperature being above a threshold temperature, the threshold temperature in a range of about 30-60° C.

5. The dual-function heat indicator of claim 1, wherein the peak exposure layer darkens in response to a peak temperature below about 60° C.

6. The dual-function heat indicator of claim 1, wherein the peak exposure layer darkens in response to a peak temperature above about 30° C.

7. The dual-function heat indicator of claim 1, further comprising a reference ring that has an appearance that is similar to the appearance of the cumulative exposure layer that has undergone the optical change in appearance.

8. The dual-function heat indicator of claim 1, further comprising a reference ring that has an appearance that is similar to the appearance of the peak exposure layer after darkening in response to a peak temperature.

9. The dual-function heat indicator of claim 1, further comprising a transparent film that overlies the cumulative exposure layer and the peak exposure layer.

10. The dual-function heat indicator of claim 1, further comprising an adhesive layer contacting the substrate on a side opposite the cumulative exposure layer and the peak exposure layer.

11. The dual-function heat indicator of claim 1, wherein the cumulative exposure layer is affected by a temperature that is below a peak temperature of the peak exposure layer.

12. The dual-function heat indicator of claim 1, wherein the cumulative exposure layer overlies the peak exposure layer.

13. The dual-function heat indicator of claim 1, wherein the cumulative exposure layer darkens in response to the cumulative heat exposure.

14. The dual-function heat indicator of claim 1, wherein the cumulative exposure layer comprises a polymerizable diacetylenic compound that darkens in response to the cumulative heat exposure.

15. The dual-function heat indicator of claim 1, wherein the meltable solid is in the form of particles configured to scatter light prior to melting, the light scattering masking a color of the particles of the meltable solid.

16. The dual-function heat indicator of claim 15, wherein melting of the meltable solid causes a color of the meltable solid to become more apparent due to a loss of light scattering.

17. The dual-function heat indicator of claim 1, wherein the peak exposure layer further comprises a colorant the color of which is masked by the meltable solid prior to melting.

18. The dual-function heat indicator of claim 17, wherein melting of the meltable solid causes the color of the colorant to become more apparent due to a loss of light scattering.

19. The dual-function heat indicator of claim 17, wherein the colorant is dissolved in particles that scatter light.

20. The dual-function heat indicator of claim 17, wherein melting of the meltable solid causes the colorant to become dissolved in the meltable solid.

21. The dual-function heat indicator of claim 1, wherein the meltable solid comprises a polymer.

22. The dual-function heat indicator of claim 21, wherein the polymer is a side-chain crystallizable polymer.

23. The dual-function heat indicator of claim 1, wherein the peak exposure layer overlies the cumulative exposure layer.

24. The dual-function heat indicator of claim 1, wherein the optical change in appearance comprises a lightening of the cumulative exposure layer.

25. The dual-function heat indicator of claim 1, wherein the meltable solid comprises an alkane, an alkyl ester, or a wax.

26. The dual-function heat indicator of claim 25, wherein the wax comprises a paraffin wax, a microcrystalline wax, carnauba wax, beeswax, Chinese wax, shellac wax, spermaceti, tallow, palm wax, soy wax, lanolin, wool grease, a waxy polymer, a waxy copolymer, a polyolefin, polyethylene, polypropylene, an ethylene-vinyl acetate copolymer, or an ethylene-acrylic acid copolymer.

27. The dual-function heat indicator of claim 1, wherein the meltable solid comprises an undecane, a dodecane, a tridecane, a tetradecane, a pentadecane, a hexadecane, a heptadecane, an octadecane, a nonadecane, an eicosane, a heneicosane, a hexanoic acid, a hexadecane or ethyl lactate.

28. The dual-function heat indicator of claim 18, wherein the colorant is in the form of particles mixed with the meltable solid.

29. The dual-function heat indicator of claim 28, wherein the meltable solid comprises a polymer.

30. The dual-function heat indicator of claim 29, wherein the polymer is a side-chain crystallizable polymer.

31. The dual-function heat indicator of claim 30, wherein the colorant is a dye.

32. The dual-function heat indicator of claim 18, wherein the colorant is encapsulated by particles of the meltable solid.

33. The dual-function heat indicator of claim 32, wherein the meltable solid comprises a polymer.

34. The dual-function heat indicator of claim 33, wherein the polymer is a side-chain crystallizable polymer.

35. The dual-function heat indicator of claim 34, wherein the colorant is a dye.

36. The dual-function heat indicator of claim 1, wherein the visual outputs of the cumulative exposure layer and the peak exposure layer are optically readable by a human viewer.

* * * * *